(12) United States Patent
Takahashi et al.

(10) Patent No.: US 10,461,099 B2
(45) Date of Patent: Oct. 29, 2019

(54) METAL OXIDE FILM AND METHOD FOR FORMING METAL OXIDE FILM

(71) Applicant: Semiconductor Energy Laboratory Co., Ltd., Atsugi-shi, Kanagawa-ken (JP)

(72) Inventors: Masahiro Takahashi, Kanagawa (JP); Takuya Hirohashi, Kanagawa (JP); Masashi Tsubuku, Kanagawa (JP); Noritaka Ishihara, Kanagawa (JP); Masashi Oota, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 50 days.

(21) Appl. No.: 15/879,506

(22) Filed: Jan. 25, 2018

(65) Prior Publication Data

US 2018/0151596 A1 May 31, 2018

Related U.S. Application Data

(63) Continuation of application No. 14/071,932, filed on Nov. 5, 2013, now Pat. No. 9,881,939.

(30) Foreign Application Priority Data

| Nov. 8, 2012 | (JP) | 2012-245992 |
| Jan. 30, 2013 | (JP) | 2013-016242 |
| Mar. 19, 2013 | (JP) | 2013-056768 |

(51) Int. Cl.
*H01L 29/10* (2006.01)
*H01L 27/12* (2006.01)
(Continued)

(52) U.S. Cl.
CPC ........ *H01L 27/1225* (2013.01); *C23C 14/086* (2013.01); *G01N 23/207* (2013.01);
(Continued)

(58) Field of Classification Search
CPC ......... H01L 21/02554; H01L 21/02565; H01L 21/02631; H01L 22/12; H01L 27/1225;
(Continued)

(56) References Cited

U.S. PATENT DOCUMENTS

| 5,731,856 A | 3/1998 | Kim et al. |
| 5,744,864 A | 4/1998 | Cillessen et al. |

(Continued)

FOREIGN PATENT DOCUMENTS

| CN | 101640220 A | 2/2010 |
| CN | 101794820 A | 8/2010 |

(Continued)

OTHER PUBLICATIONS

Korean Office Action (Application No. 2018-7022703) dated Oct. 31, 2018.
(Continued)

*Primary Examiner* — Brook Kebede
(74) *Attorney, Agent, or Firm* — Fish & Richardson P.C.

(57) ABSTRACT

A metal oxide film including a crystal part and having highly stable physical properties is provided. The size of the crystal part is less than or equal to 10 nm, which allows the observation of circumferentially arranged spots in a nano-beam electron diffraction pattern of the cross section of the metal oxide film when the measurement area is greater than or equal to 5 nmφ and less than or equal to 10 nmφ.

19 Claims, 24 Drawing Sheets

(51) Int. Cl.
   *H01L 29/04* (2006.01)
   *H01L 21/66* (2006.01)
   *H01L 29/24* (2006.01)
   *G02F 1/1368* (2006.01)
   *G01N 23/207* (2018.01)
   *C23C 14/08* (2006.01)
   *H01L 29/66* (2006.01)
   *H01L 29/786* (2006.01)
   *H01L 21/02* (2006.01)

(52) U.S. Cl.
   CPC ............ *G02F 1/1368* (2013.01); *H01L 22/12* (2013.01); *H01L 29/04* (2013.01); *H01L 29/24* (2013.01); *H01L 29/66969* (2013.01); *H01L 29/7869* (2013.01); *H01L 29/78693* (2013.01); *H01L 21/0237* (2013.01); *H01L 21/02422* (2013.01); *H01L 21/02554* (2013.01); *H01L 21/02565* (2013.01); *H01L 21/02631* (2013.01); *H01L 2924/0002* (2013.01)

(58) Field of Classification Search
   CPC ... H01L 29/04; H01L 29/24; H01L 29/66969; H01L 29/7869; H01L 29/78693; H01L 29/78696; C23C 14/0021; C23C 14/086; C23C 14/28; C23C 14/3414
   USPC ........................................................ 257/43
   See application file for complete search history.

(56) References Cited

U.S. PATENT DOCUMENTS

| | | |
|---|---|---|
| 6,294,274 B1 | 9/2001 | Kawazoe et al. |
| 6,563,174 B2 | 5/2003 | Kawasaki et al. |
| 6,727,522 B1 | 4/2004 | Kawasaki et al. |
| 7,049,190 B2 | 5/2006 | Takeda et al. |
| 7,061,014 B2 | 6/2006 | Hosono et al. |
| 7,064,346 B2 | 6/2006 | Kawasaki et al. |
| 7,105,868 B2 | 9/2006 | Nause et al. |
| 7,211,825 B2 | 5/2007 | Shih et al. |
| 7,282,782 B2 | 10/2007 | Hoffman et al. |
| 7,291,826 B2 | 11/2007 | Vaillant |
| 7,297,977 B2 | 11/2007 | Hoffman et al. |
| 7,323,356 B2 | 1/2008 | Hosono et al. |
| 7,385,224 B2 | 6/2008 | Ishii et al. |
| 7,402,506 B2 | 7/2008 | Levy et al. |
| 7,411,209 B2 | 8/2008 | Endo et al. |
| 7,453,065 B2 | 11/2008 | Saito et al. |
| 7,453,087 B2 | 11/2008 | Iwasaki |
| 7,462,862 B2 | 12/2008 | Hoffman et al. |
| 7,468,304 B2 | 12/2008 | Kaji et al. |
| 7,501,293 B2 | 3/2009 | Ito et al. |
| 7,601,984 B2 | 10/2009 | Sano et al. |
| 7,674,650 B2 | 3/2010 | Akimoto et al. |
| 7,732,819 B2 | 6/2010 | Akimoto et al. |
| 7,767,106 B2 | 8/2010 | Chang |
| 7,935,964 B2 | 5/2011 | Kim et al. |
| 7,998,372 B2 | 8/2011 | Yano et al. |
| 8,168,544 B2 | 5/2012 | Chang |
| 8,193,045 B2 | 6/2012 | Omura et al. |
| 8,207,756 B2 | 6/2012 | Shionoiri et al. |
| 8,236,635 B2 | 8/2012 | Suzawa et al. |
| 8,242,494 B2 | 8/2012 | Suzawa et al. |
| 8,293,595 B2 | 10/2012 | Yamazaki et al. |
| 8,304,765 B2 | 11/2012 | Yamazaki et al. |
| 8,309,961 B2 | 11/2012 | Yamazaki et al. |
| 8,319,215 B2 | 11/2012 | Yamazaki et al. |
| 8,319,218 B2 | 11/2012 | Yamazaki et al. |
| 8,329,506 B2 | 12/2012 | Akimoto et al. |
| 8,343,799 B2 | 1/2013 | Ito et al. |
| 8,384,080 B2 | 2/2013 | Taniguchi et al. |
| 8,536,571 B2 | 9/2013 | Yamazaki |
| 8,557,641 B2 | 10/2013 | Sasaki et al. |
| 8,624,237 B2 | 1/2014 | Yamazaki et al. |
| 8,629,432 B2 | 1/2014 | Sakata et al. |
| 8,643,011 B2 | 2/2014 | Akimoto et al. |
| 8,686,416 B2 | 4/2014 | Honda et al. |
| 8,704,216 B2 | 4/2014 | Godo et al. |
| 8,835,921 B2 | 9/2014 | Honda et al. |
| 8,841,710 B2 | 9/2014 | Yamazaki et al. |
| 8,846,460 B2 | 9/2014 | Sasaki et al. |
| 8,884,287 B2 | 11/2014 | Sakata et al. |
| 9,048,094 B2 | 6/2015 | Miyanaga et al. |
| 9,048,144 B2 | 6/2015 | Yamazaki et al. |
| 9,064,899 B2 | 6/2015 | Godo et al. |
| 9,166,026 B2 | 10/2015 | Yamazaki |
| 9,196,690 B2 | 11/2015 | Honda et al. |
| 9,252,288 B2 | 2/2016 | Akimoto et al. |
| 9,306,072 B2 | 4/2016 | Yamazaki et al. |
| 9,520,288 B2 | 12/2016 | Miyanaga et al. |
| 9,660,102 B2 | 5/2017 | Godo et al. |
| 9,666,719 B2 | 5/2017 | Yamazaki et al. |
| 2001/0046027 A1 | 11/2001 | Tai et al. |
| 2002/0000593 A1 | 1/2002 | Nishiyama et al. |
| 2002/0028541 A1 | 3/2002 | Lee et al. |
| 2002/0056838 A1 | 5/2002 | Ogawa |
| 2002/0132454 A1 | 9/2002 | Ohtsu et al. |
| 2003/0006373 A1 | 1/2003 | Koguchi et al. |
| 2003/0189401 A1 | 10/2003 | Kido et al. |
| 2003/0218222 A1 | 11/2003 | Wager, III et al. |
| 2004/0038446 A1 | 2/2004 | Takeda et al. |
| 2004/0067659 A1 | 4/2004 | Black et al. |
| 2004/0127038 A1 | 7/2004 | Carcia et al. |
| 2005/0017302 A1 | 1/2005 | Hoffman |
| 2005/0199959 A1 | 9/2005 | Chiang et al. |
| 2006/0035452 A1 | 2/2006 | Carcia et al. |
| 2006/0043377 A1 | 3/2006 | Hoffman et al. |
| 2006/0091793 A1 | 5/2006 | Baude et al. |
| 2006/0108529 A1 | 5/2006 | Saito et al. |
| 2006/0108636 A1 | 5/2006 | Sano et al. |
| 2006/0110867 A1 | 5/2006 | Yabuta et al. |
| 2006/0113536 A1 | 6/2006 | Kumomi et al. |
| 2006/0113539 A1 | 6/2006 | Sano et al. |
| 2006/0113549 A1 | 6/2006 | Den et al. |
| 2006/0113565 A1 | 6/2006 | Abe et al. |
| 2006/0169973 A1 | 8/2006 | Isa et al. |
| 2006/0170111 A1 | 8/2006 | Isa et al. |
| 2006/0197092 A1 | 9/2006 | Hoffman et al. |
| 2006/0208977 A1 | 9/2006 | Kimura |
| 2006/0228974 A1 | 10/2006 | Thelss et al. |
| 2006/0231882 A1 | 10/2006 | Kim et al. |
| 2006/0238135 A1 | 10/2006 | Kimura |
| 2006/0244107 A1 | 11/2006 | Sugihara et al. |
| 2006/0284171 A1 | 12/2006 | Levy et al. |
| 2006/0284172 A1 | 12/2006 | Ishii |
| 2006/0292777 A1 | 12/2006 | Dunbar |
| 2007/0024187 A1 | 2/2007 | Shin et al. |
| 2007/0046191 A1 | 3/2007 | Saito |
| 2007/0052025 A1 | 3/2007 | Yabuta |
| 2007/0054507 A1 | 3/2007 | Kaji et al. |
| 2007/0090365 A1 | 4/2007 | Hayashi et al. |
| 2007/0108446 A1 | 5/2007 | Akimoto |
| 2007/0152217 A1 | 7/2007 | Lai et al. |
| 2007/0154561 A1 | 7/2007 | Takeda et al. |
| 2007/0172591 A1 | 7/2007 | Seo et al. |
| 2007/0187678 A1 | 8/2007 | Hirao et al. |
| 2007/0187760 A1 | 8/2007 | Furuta et al. |
| 2007/0194379 A1 | 8/2007 | Hosono et al. |
| 2007/0252928 A1 | 11/2007 | Ito et al. |
| 2007/0272922 A1 | 11/2007 | Kim et al. |
| 2007/0287296 A1 | 12/2007 | Chang |
| 2008/0006877 A1 | 1/2008 | Mardilovich et al. |
| 2008/0008908 A1 | 1/2008 | Ishiwata et al. |
| 2008/0038882 A1 | 2/2008 | Takechi et al. |
| 2008/0038929 A1 | 2/2008 | Chang |
| 2008/0050595 A1 | 2/2008 | Nakagawara et al. |
| 2008/0073653 A1 | 3/2008 | Iwasaki |
| 2008/0083950 A1 | 4/2008 | Pan et al. |
| 2008/0106191 A1 | 5/2008 | Kawase |
| 2008/0128689 A1 | 6/2008 | Lee et al. |
| 2008/0129195 A1 | 6/2008 | Ishizaki et al. |
| 2008/0166834 A1 | 7/2008 | Kim et al. |
| 2008/0180544 A1 | 7/2008 | Drader et al. |

(56) References Cited

U.S. PATENT DOCUMENTS

| | | | |
|---|---|---|---|
| 2008/0182358 | A1 | 7/2008 | Cowdery-Corvan et al. |
| 2008/0224133 | A1 | 9/2008 | Park et al. |
| 2008/0254569 | A1 | 10/2008 | Hoffman et al. |
| 2008/0258139 | A1 | 10/2008 | Ito et al. |
| 2008/0258140 | A1 | 10/2008 | Lee et al. |
| 2008/0258141 | A1 | 10/2008 | Park et al. |
| 2008/0258143 | A1 | 10/2008 | Kim et al. |
| 2008/0296568 | A1 | 12/2008 | Ryu et al. |
| 2009/0008638 | A1 | 1/2009 | Kang et al. |
| 2009/0068773 | A1 | 3/2009 | Lai et al. |
| 2009/0073325 | A1 | 3/2009 | Kuwabara et al. |
| 2009/0114910 | A1 | 5/2009 | Chang |
| 2009/0134389 | A1 | 5/2009 | Matsunaga |
| 2009/0134399 | A1 | 5/2009 | Sakakura et al. |
| 2009/0152506 | A1 | 6/2009 | Umeda et al. |
| 2009/0152541 | A1 | 6/2009 | Maekawa et al. |
| 2009/0179199 | A1 | 7/2009 | Sano et al. |
| 2009/0278122 | A1 | 11/2009 | Hosono et al. |
| 2009/0280600 | A1 | 11/2009 | Hosono et al. |
| 2010/0015164 | A1 | 1/2010 | Clemens et al. |
| 2010/0025676 | A1 | 2/2010 | Yamazaki et al. |
| 2010/0051949 | A1 | 3/2010 | Yamazaki et al. |
| 2010/0055832 | A1 | 3/2010 | Akimoto et al. |
| 2010/0065839 | A1 | 3/2010 | Yamazaki et al. |
| 2010/0065840 | A1 | 3/2010 | Yamazaki et al. |
| 2010/0065844 | A1 | 3/2010 | Tokunaga |
| 2010/0072467 | A1 | 3/2010 | Yamazaki et al. |
| 2010/0084650 | A1 | 4/2010 | Yamazaki et al. |
| 2010/0092800 | A1 | 4/2010 | Itagaki et al. |
| 2010/0102312 | A1 | 4/2010 | Yamazaki et al. |
| 2010/0105163 | A1 | 4/2010 | Ito et al. |
| 2010/0105164 | A1 | 4/2010 | Ito et al. |
| 2010/0109002 | A1 | 5/2010 | Itagaki et al. |
| 2010/0117075 | A1 | 5/2010 | Akimoto et al. |
| 2010/0123136 | A1 | 5/2010 | Lee et al. |
| 2010/0193782 | A1 | 8/2010 | Sakata |
| 2010/0301329 | A1 | 12/2010 | Asano et al. |
| 2011/0062433 | A1 | 3/2011 | Yamazaki |
| 2011/0062436 | A1 | 3/2011 | Yamazaki et al. |
| 2011/0117698 | A1 | 5/2011 | Suzawa et al. |
| 2011/0227060 | A1 | 9/2011 | Miyanaga et al. |
| 2011/0306165 | A1* | 12/2011 | Ikisawa .............. C04B 35/453 438/104 |
| 2012/0138922 | A1 | 6/2012 | Yamazaki et al. |
| 2012/0211745 | A1 | 8/2012 | Ueda et al. |
| 2012/0228608 | A1* | 9/2012 | Yano .............. C01G 15/006 257/43 |
| 2012/0241735 | A1 | 9/2012 | Honda et al. |
| 2012/0256179 | A1 | 10/2012 | Yamazaki et al. |
| 2012/0267624 | A1 | 10/2012 | Isobe et al. |
| 2012/0273780 | A1 | 11/2012 | Yamazaki et al. |
| 2012/0276694 | A1 | 11/2012 | Koezuka et al. |
| 2012/0321039 | A1 | 12/2012 | Bare et al. |
| 2013/0075723 | A1 | 3/2013 | Yamazaki et al. |
| 2013/0099229 | A1 | 4/2013 | Wakana et al. |
| 2013/0214273 | A1 | 8/2013 | Yamazaki et al. |
| 2013/0264565 | A1 | 10/2013 | Nishimura et al. |
| 2014/0377907 | A1 | 12/2014 | Sasaki et al. |
| 2015/0060850 | A1 | 3/2015 | Yamazaki et al. |
| 2015/0179676 | A1 | 6/2015 | Yamazaki et al. |
| 2015/0270405 | A1 | 9/2015 | Takahashi et al. |
| 2015/0294994 | A1 | 10/2015 | Takahashi et al. |
| 2016/0111282 | A1 | 4/2016 | Akimoto et al. |
| 2017/0236943 | A1 | 8/2017 | Yamazaki et al. |

FOREIGN PATENT DOCUMENTS

| | | |
|---|---|---|
| CN | 102484135 A | 5/2012 |
| DE | 112011104002 | 8/2013 |
| EP | 1737044 A | 12/2006 |
| EP | 2226847 A | 9/2010 |
| EP | 2544237 A | 1/2013 |
| EP | 3249698 A | 11/2017 |
| JP | 60-198861 A | 10/1985 |
| JP | 63-210022 A | 8/1988 |
| JP | 63-210023 A | 8/1988 |
| JP | 63-210024 A | 8/1988 |
| JP | 63-215519 A | 9/1988 |
| JP | 63-239117 A | 10/1988 |
| JP | 63-265818 A | 11/1988 |
| JP | 05-251705 A | 9/1993 |
| JP | 08-264794 A | 10/1996 |
| JP | 11-505377 | 5/1999 |
| JP | 2000-044236 A | 2/2000 |
| JP | 2000-150900 A | 5/2000 |
| JP | 2002-016063 A | 1/2002 |
| JP | 2002-076356 A | 3/2002 |
| JP | 2002-289859 A | 10/2002 |
| JP | 2003-086000 A | 3/2003 |
| JP | 2003-086808 A | 3/2003 |
| JP | 2004-103957 A | 4/2004 |
| JP | 2004-273614 A | 9/2004 |
| JP | 2004-273732 A | 9/2004 |
| JP | 2006-054469 A | 2/2006 |
| JP | 2006-165529 A | 6/2006 |
| JP | 2006-261483 A | 9/2006 |
| JP | 2008-042067 A | 2/2008 |
| JP | 2009-010362 A | 1/2009 |
| JP | 2010-056540 A | 3/2010 |
| JP | 2010-058135 A | 3/2010 |
| JP | 2010-103451 A | 5/2010 |
| JP | 2010-226101 A | 10/2010 |
| JP | 2011-029630 A | 2/2011 |
| JP | 2011-100979 A | 5/2011 |
| JP | 2011-138934 A | 7/2011 |
| JP | 2012-023880 A | 2/2012 |
| JP | 2012-134475 A | 7/2012 |
| JP | 2012-144431 A | 8/2012 |
| JP | 2012-186383 A | 9/2012 |
| JP | 2013-102171 A | 5/2013 |
| JP | 2013-149994 A | 8/2013 |
| JP | 2013-149995 A | 8/2013 |
| JP | 2014-205902 A | 10/2014 |
| KR | 2010-0056970 A | 5/2010 |
| KR | 2011-0065556 A | 6/2011 |
| KR | 2012-0046302 A | 5/2012 |
| KR | 2012-0056870 A | 6/2012 |
| KR | 2012-0090784 A | 8/2012 |
| KR | 2012-0109350 A | 10/2012 |
| TW | 201023357 | 6/2010 |
| TW | 201222825 | 6/2012 |
| TW | 201236157 | 9/2012 |
| TW | 201244113 | 11/2012 |
| TW | 201244114 | 11/2012 |
| WO | WO-2004/114391 | 12/2004 |
| WO | WO-2006/054469 | 5/2006 |
| WO | WO-2007/058231 | 5/2007 |
| WO | WO-2008/149873 | 12/2008 |
| WO | WO-2010/038820 | 4/2010 |
| WO | WO-2011/001879 | 1/2011 |
| WO | WO-2011/027467 | 3/2011 |
| WO | WO-2011/033936 | 3/2011 |
| WO | WO-2011/037050 | 3/2011 |
| WO | WO-2011/043176 | 4/2011 |
| WO | WO-2011/132769 | 10/2011 |
| WO | WO-2012/073844 | 6/2012 |
| WO | WO-2014/073585 | 5/2014 |

OTHER PUBLICATIONS

Asakuma.N et al., "Crystallization and Reduction of SOL-Gel-Derived Zinc Oxide Films by Irradiation With Ultraviolet Lamp", Journal of SOL-Gel Science and Technology, 2003, vol. 26, pp. 181-184.

Asaoka.Y et al., "29.1:Polarizer-Free Reflective LCD Combined With Ultra Low-Power Driving Technology", SID Digest '09 : SID International Symposium Digest of Technical Papers, May 31, 2009, pp. 395-398.

Chern.H et al., "An Analytical Model for the Above-Threshold Characteristics of Polysilicon Thin-Film Transistors", IEEE Transactions on Electron Devices, Jul. 1, 1995, vol. 42, No. 7, pp. 1240-1246.

(56) References Cited

OTHER PUBLICATIONS

Cho.D et al., "21.2:Al and Sn-Doped Zinc Indium Oxide Thin Film Transistors for AMOLED Back Plane", SID Digest '09 : SID International Symposium Digest of Technical Papers, May 31, 2009, pp. 280-283.

Clark.S et al., "First Principles Methods Using CASTEP", Zeitschrift fur Kristallographie, 2005, vol. 220, pp. 567-570.

Coates.D et al., "Optical Studies of the Amorphous Liquid-Cholesteric Liquid Crystal Transition:The "Blue Phase"", Physics Letters, Sep. 10, 1973, vol. 45A, No. 2, pp. 115-116.

Costello.M et al., "Electron Microscopy of a Cholesteric Liquid Crystal and Its Blue Phase", Phys. Rev. A (Physical Review. A), May 1, 1984, vol. 29, No. 5, pp. 2957-2959.

Dembo.H et al., "RFCPUS on Glass and Plastic Substrates Fabricated by TFT Transfer Technology", IEDM 05: Technical Digest of International Electron Devices Meeting, Dec. 5, 2005, pp. 1067-1069.

Fortunato.E et al., "Wide-Bandgap High-Mobility ZNO Thin-Film Transistors Produced at Room Temperature", Appl. Phys. Lett. (Applied Physics Letters) , Sep. 27, 2004, vol. 85, No. 13, pp. 2541-2543.

Fung.T et al., "2-D Numerical Simulation of High Performance Amorphous In—Ga—Zn—O TFTs for Flat Panel Displays", AM-FPD '08 Digest of Technical Papers, Jul. 2, 2008, pp. 251-252, The Japan Society of Applied Physics.

Godo.H et al., "P-9:Numerical Analysis on Temperature Dependence of Characteristics of Amorphous In—Ga—Zn-Oxide TFT", SID Digest '09 : SID International Symposium Digest of Technical Papers, May 31, 2009, pp. 1110-1112.

Godo.H et al., "Temperature Dependence of Characteristics and Electronic Structure for Amorphous In—Ga—Zn-Oxide TFT", AM-FPD '09 Digest of Technical Papers, Jul. 1, 2009, pp. 41-44.

Hayashi.R et al., "42.1: Invited Paper: Improved Amorphous In—Ga—Zn—O Tfts", SID Digest '08 : SID International Symposium Digest of Technical Papers, May 20, 2008, vol. 39, pp. 621-624.

Hirao.T et al., "Novel Top-Gate Zinc Oxide Thin-Film Transistors (ZNO TFTS) for AMLCDS", J. Soc. Inf. Display (Journal of the Society for Information Display), 2007, vol. 15, No. 1, pp. 17 22.

Hosono.H et al., "Working hypothesis to explore novel wide band gap electrically conducting amorphous oxides and examples", J. Non-Cryst. Solids (Journal of Non-Crystalline Solids), 1996, vol. 198-200, pp. 165-169.

Hosono.H, "68.3:Invited Paper:Transparent Amorphous Oxide Semiconductors for High Performance TFT", SID Digest '07 : SID International Symposium Digest of Technocal Papers, 2007, vol. 38, pp. 1830-1833.

Hsieh.H et al., "P-29:Modeling of Amorphous Oxide Semiconductor Thin Film Transistors and Subgap Density of States", SID Digest '08 : SID International Symposium Digest of Technical Papers, May 20, 2008, vol. 39, pp. 1277-1280.

Ikeda.T et al., "Full-Functional System Liquid Crystal Display Using CG-Silicon Technology", SID Digest '04 : SID International Symposium Digest of Technical Papers, 2004, vol. 35, pp. 860-863.

Janotti.A et al., "Native Point Defects in ZnO", Phys. Rev. B (Physical Review. B), Oct. 4, 2007, vol. 76, No. 16, pp. 165202-1-165202-22.

Janotti.A et al., "Oxygen Vacancies in ZnO", Appl. Phys. Lett. (Applied Physics Letters) , 2005, vol. 87, pp. 122102-1-122102-3.

Jeong.J et al., "3.1: Distinguished Paper: 12.1-Inch WXGA AMOLED Display Driven by Indium-Gallium-Zinc Oxide TFTs Array", SID Digest '08 : SID International Symposium Digest of Technical Papers, May 20, 2008, vol. 39, No. 1, pp. 1-4.

Jin.D et al., "65.2:Distinguished Paper:World-Largest (6.5") Flexible Full Color Top Emission AMOLED Display on Plastic Film and its Bending Properties", SID Digest '09 : SID International Symposium Digest of Technical Papers, May 31, 2009, pp. 983-985.

Kanno.H et al., "White Stacked Electrophosphorecent Organic Light-Emitting Devices Emplying MOO3 as a Charge-Generation Layer", Adv. Mater. (Advanced Materials), 2006, vol. 18, No. 3, pp. 399-342.

Kikuchi.H et al., "39.1:Invited Paper:Optically Isotropic Nano-Structured Liquid Crystal Composites for Display Applications", SID Digest '09 : SID International Symposium Digest of Technical Papers, May 31, 2009, pp. 578-581.

Kikuchi.H et al., "62.2: Invited Paper:Fast Electro-Optical Switching in Polymer-Stabilized Liquid Crystalline Blue Phases for Display Application", SID Digest '07 : SID International Symposium Digest of Technical Papers, 2007, vol. 38, pp. 1737-1740.

Kikuchi.H et al., "Polymer-Stabilized Liquid Crystal Blue Phases", Nature Materials, Sep. 2, 2002, vol. 1, pp. 64-68.

Kim.S et al., "High-Performance oxide thin film transistors passivated by various gas plasmas", 214th ECS Meeting, 2008, No. 2317, ECS.

Kimizuka.N et al., "Spinel,YbFe2O4, and Yb2Fe3O7 Types of Structures for Compounds in the In2O3 and Sc2O3-A2O3-BO Systems [A; Fe, Ga, or Al; B: Mg, Fe, Ni, Cu, or Zn] at Temperatures Over 1000° C.", Journal of Solid State Chemistry, 1985, vol. 60, pp. 382-384.

Kimizuka.N et al., "Syntheses and Single-Crystal Data of Homologous Compounds, In2O3(ZnO)m (m=3, 4, and 5), InGaO3(ZnO)3, and Ga2O3(ZnO)m (m=7, 8, 9, and 16) in the In2O3—ZnGa2O4—ZnO System", Journal of Solid State Chemistry, Apr. 1, 1995, vol. 116, No. 1, pp. 170-178.

Kitzerow.H et al., "Observation of Blue Phases in Chiral Networks", Liquid Crystals, 1993, vol. 14, No. 3, pp. 911-916.

Kurokawa.Y et al., "UHF RFCPUS on Flexible and Glass Substrates for Secure RFID Systems", Journal of Solid-State Circuits , 2008, vol. 43, No. 1, pp. 292-299.

Lany.S et al., "Dopability, Intrinsic Conductivity, and Nonstoichiometry of Transparent Conducting Oxides", Phys. Rev. Lett. (Physical Review Letters), Jan. 26, 2007, vol. 98, pp. 045501-1-045501-4.

Lee.H et al., "Current Status of, Challenges to, and Perspective View of AM-OLED ", IDW '06 : Proceedings of the 13th International Display Workshops, Dec. 7, 2006, pp. 663-666.

Lee.J et al., "World's Largest (15-Inch) XGA AMLCD Panel Using IGZO Oxide TFT", SID Digest '08 : SID International Symposium Digest of Technical Papers, May 20, 2008, vol. 39, pp. 625-628.

Lee.M et al., "15.4:Excellent Performance of Indium-Oxide-Based Thin-Film Transistors by DC Sputtering", SID Digest '09 : SID International Syposium Digest of Technical Papers, May 31, 2009, pp. 191-193.

Li.C et al., "Modulated Structures of Homologous Compounds InMO3(ZnO)m (M=In,Ga; m=Integer) Described by Four-Dimensional Superspace Group", Journal of Solid State Chemistry, 1998, vol. 139, pp. 347-355.

Masuda.S et al., "Transparent thin film transistors using ZnO as an active channel layer and their electrical properties", J. Appl. Phys. (Journal of Applied Physics) , Feb. 1, 2003, vol. 93, No. 3, pp. 1624-1630.

Meiboom.S et al., "Theory of the Blue Phase of Cholesteric Liquid Crystals", Phys. Rev. Lett. (Physical Review Letters), May 4, 1981, vol. 46, No. 18, pp. 1216-1219.

Miyasaka.M, "Suftla Flexible Microelectronics on Their Way to Business", SID Digest '07 : SID International Symposium Digest of Technical Papers, 2007, vol. 38, pp. 1673-1676.

Mo.Y et al., "Amorphous Oxide TFT Backplanes for Large Size AMOLED Displays", IDW '08 : Proceedings of the 6th International Display Workshops, Dec. 3, 2008, pp. 581-584.

Nakamura.M et al., "The phase relations in the In2O3—Ga2ZnO4—ZnO system at 1350° C.", Journal of Solid State Chemistry, Aug. 1, 1991, vol. 93, No. 2, pp. 298-315.

Nakamura.M, "Synthesis of Homologous Compound with New Long-Period Structure", NIRIM Newsletter, Mar. 1, 1995, vol. 150, pp. 1-4.

Nomura.K et al., "Amorphous Oxide Semiconductors for High-Performance Flexible Thin-Film Transistors", Jpn. J. Appl. Phys. (Japanese Journal of Applied Physics) , 2006, vol. 45, No. 5B, pp. 4303-4308.

Nomura.K et al., "Carrier transport in transparent oxide semiconductor with intrinsic structural randomness probed using single-crystalline InGaO3(ZnO)5 films", Appl. Phys. Lett. (Applied Physics Letters) , Sep. 13, 2004, vol. 85, No. 11, pp. 1993-1995.

(56) References Cited

OTHER PUBLICATIONS

Nomura.K et al., "Room-Temperature Fabrication of Transparent Flexible Thin-Film Transistors Using Amorphous Oxide Semiconductors", Nature, Nov. 25, 2004, vol. 432, pp. 488-492.
Nomura.K et al., "Thin-Film Transistor Fabricated in Single-Crystalline Transparent Oxide Semiconductor", Science, May 23, 2003, vol. 300, No. 5623, pp. 1269-1272.
Nowatari.H et al., "60.2: Intermediate Connector With Suppressed Voltage Loss for White Tandem OLEDS", SID Digest '09 : SID International Symposium Digest of Technical Papers, May 31, 2009, vol. 40, pp. 899-902.
Oba.F et al., "Defect energetics in ZnO: A hybrid Hartree-Fock density functional study", Phys. Rev. B (Physical Review. B), 2008, vol. 77, pp. 245202-1-245202-6.
Oh.M et al., "Improving the Gate Stability of ZNO Thin-Film Transistors With Aluminum Oxide Dielectric Layers", J. Electrochem. Soc. (Journal of Electrochemical Society), 2008, vol. 155, No. 12, pp. H1009-H1014.
Ohara.H et al., "21.3:4.0 In. QVGA AMOLED Display Using In—Ga—Zn-Oxide TFTS With a Novel Passivation Layer", SID Digest '09 : SID International Symposium Digest of Technical Papers, May 31, 2009, pp. 284-287.
Ohara.H et al., "Amorphous In—Ga—Zn-Oxide TFTs with Suppressed Variation for 4.0 inch QVGA AMOLED Display", AM-FPD '09 Digest of Technical Papers, Jul. 1, 2009, pp. 227-230, The Japan Society of Applied Physics.
Orita.M et al., "Amorphous transparent conductive oxide InGaO3(ZnO)m (m<4):a Zn4s conductor", Philosophical Magazine, 2001, vol. 81, No. 5, pp. 501-515.
Orita.M et al., "Mechanism of Electrical Conductivity of Transparent InGaZnO4", Phys. Rev B (Physical Review. B), Jan. 15, 2000, vol. 61, No. 3, pp. 1811-1816.
Osada.T et al., "15.2: Development of Driver-Integrated Panel using Amorphous In—Ga—Zn-Oxide TFT", SID Digest '09 : SID International Symposium Digest of Technical Papers, May 31, 2009, vol. 40, pp. 184-187.
Osada.T et al., "Development of Driver-Integrated Panel Using Amorphous In—Ga—Zn-Oxide TFT", AM-FPD '09 Digest of Technical Papers, Jul. 1, 2009, pp. 33-36.
Park.J et al., "Amorphous Indium-Gallium-Zinc Oxide TFTS and Their Application for Large Size AMOLED", AM-FPD '08 Digest of Technical Papers, Jul. 2, 2008, pp. 275-278.
Park.J et al., "Dry etching of ZnO films and plasma-induced damage to optical properties", J. Vac. Sci. Technol. B (Journal of Vacuum Science & Technology B), Mar. 1, 2003, vol. 21, No. 2, pp. 800-803.
Park.J et al., "Electronic Transport Properties of Amorphous Indium-Gallium-Zinc Oxide Semiconductor Upon Exposure to Water", Appl. Phys. Lett. (Applied Physics Letters) , 2008, vol. 92, pp. 072104-1-072104-3.
Park.J et al., "High performance amorphous oxide thin film transistors with self-aligned top-gate structure", IEDM 09: Technical Digest of International Electron Devices Meeting, Dec. 7, 2009, pp. 191-194.
Park.J et al., "Improvements in the Device Characteristics of Amorphous Indium Gallium Zinc Oxide Thin-Film Transistors by Ar Plasma Treatment", Appl. Phys. Lett. (Applied Physics Letters) , Jun. 26, 2007, vol. 90, No. 26, pp. 262106-1-262106-3.
Park.S et al., "Challenge to Future Displays: Transparent AM-OLED Driven by PEALD Grown ZNO TFT", IMID '07 Digest, 2007, pp. 1249-1252.
Park.S et al., "42.3: Transparent ZnO Thin Film Transistor for the Application of High Aperture Ratio Bottom Emission AM-OLED Display", SID Digest '08 : SID International Symposium Digest of Technical Papers, May 20, 2008, vol. 39, pp. 629-632.
Prins.M et al., "A Ferroelectric Transparent Thin-Film Transistor", Appl. Phys. Lett. (Applied Physics Letters) , Jun. 17, 1996, vol. 68, No. 25, pp. 3650-3652.
Sakata.J et al., "Development of 4.0-In. AMOLED Display With Driver Circuit Using Amorphous In—Ga—Zn-Oxide TFTS", IDW '09 : Proceedings of The 16th International Display Workshops, 2009, pp. 689-692.
Son.K et al., "42.4L: Late-News Paper: 4 Inch QVGA AMOLED Driven by the Threshold Voltage Controled Amorphous GIZO (Ga2O3—In2O3—ZnO) TFT", SID Digest '08 : SID International Symposium Digest of Technical Papers, May 20, 2008, vol. 39, pp. 633-636.
Takahashi.M et al., "Theoretical Analysis of IGZO Transparent Amorphous Oxide Semiconductor", IDW '08 : Proceedings of the 15th International Display Workshops, Dec. 3, 2008, pp. 1637-1640.
Tsuda.K et al., "Ultra Low Power Consumption Technologies for Mobile TFT-LCDs", IDW '02 : Proceedings of the 9th International Display Workshops, Dec. 4, 2002, pp. 295-298.
Ueno.K et al., "Field-Effect Transistor on SrTiO3 With Sputtered Al2O3 Gate Insulator", Appl. Phys. Lett. (Applied Physics Letters) , Sep. 1, 2003, vol. 83, No. 9, pp. 1755-1757.
Van de Walle.C, "Hydrogen as a Cause of Doping in Zinc Oxide", Phys. Rev. Lett. (Physical Review Letters), Jul. 31, 2000, vol. 85, No. 5, pp. 1012-1015.
International Search Report (Application No. PCT/JP2013/080062) dated Dec. 24, 2013.
Written Opinion (Application No. PCT/JP2013/080062) dated Dec. 24, 2013.
Matteucci.G et al., "An experiment on the particle-wave nature of electrons", Eur. J. Phys (European Journal of Physics), 2009, vol. 30, pp. 217-226.
Korean Office Action (Application No. 2016-7008650) dated Apr. 21, 2016.
Taiwanese Office Action (Application No. 105113977) dated Jul. 1, 2016.
Zhu.Y et al., "Analytical chemistry of materials", Academic Library of China Talent fund, Jul. 31, 2009, pp. 177-182, Chemical Industry Press.
Chinese Office Action (Application No. 201380058422.8) dated Oct. 10, 2016.
German Office Action (Application No. 112013007539.3) dated Dec. 19, 2016.
Kumar.C, "11.3 Incorporation of Quantum Dots in Glass Beads for Bioapplications", Semiconductor Nanomaterials, 2010, p. 413, WILEY.
Singh.M et al., "Nanointegration: Patterning, Positioning and Self-Assembly", Ceramic Integration and Joining Technologies, 2011, p. 546, WILEY.
"Cleanrooms and associated controlled environments—Part3: Test methods", Japanese Industrial Standard, Mar. 20, 2009, p. 1,50.
Allowed Claims from Japanese Patent No. JP-5894694, dated Mar. 30, 2016.
Korean Office Action (Application No. 2016-7008650) dated Apr. 10, 2017.
Wang.Z.L., "Lattice imaging using plasmon energy-loss electrons in an energy-filtered transmission electron microscope", Ultramicroscopy, 1997, vol. 67, pp. 105-111, ELSEVIER.
Zhang.Y, Research Methodology of Inorganic Non-metallic Materials, Jun. 30, 2011, p. 128, Metallurgical Industry Press.
Dong.Y et al., Research Methodology of Polymer, Apr. 30, 2011, pp. 199-203, China Petrochemistry Press.
Chinese Office Action (Application No. 201380058422.8) dated Nov. 27, 2017.

\* cited by examiner 50 nm 10 nm

FIG. 22
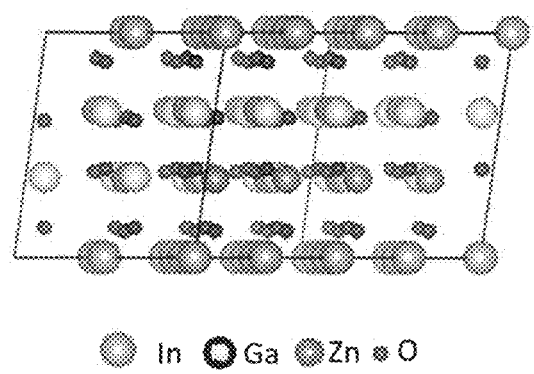
FIG. 23A      FIG. 23B
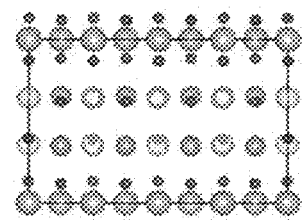   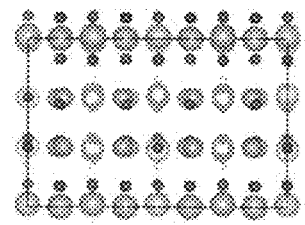
FIG. 23C      FIG. 23D
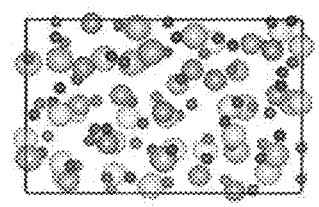   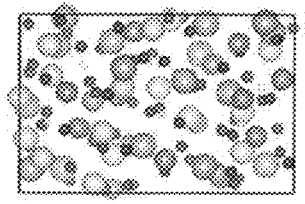

METAL OXIDE FILM AND METHOD FOR FORMING METAL OXIDE FILM

CROSS-REFERENCE TO RELATED APPLICATIONS

This application is a continuation of U.S. application Ser. No. 14/071,932, filed Nov. 5, 2013, now allowed, which claims the benefit of foreign priority applications filed in Japan as Serial No. 2012-245992 on Nov. 8, 2012, Serial No. 2013-016242 on Jan. 30, 2013, and Serial No. 2013-056768 on Mar. 19, 2013, all of which are incorporated by reference.

TECHNICAL FIELD

One embodiment of the present invention relates to, for example, a semiconductor device, a display device, a light-emitting device, a driving method thereof, or a manufacturing method thereof. One embodiment of the present invention particularly relates to a metal oxide film and a method for forming the metal oxide film. Further, one embodiment of the present invention relates to a semiconductor device including the metal oxide film.

Note that a semiconductor device in this specification and the like refers to any device that can function by utilizing semiconductor characteristics, and for example, electro-optical devices, semiconductor circuits, and electronic devices are all semiconductor devices.

BACKGROUND ART

A technique by which a transistor is formed using a semiconductor thin film formed over a substrate having an insulating surface has been attracting attention. Such a transistor is applied to a wide range of electronic devices such as an integrated circuit (IC) and an image display device (also simply referred to as a display device). As a semiconductor film applicable to the transistor, a silicon-based semiconductor material is widely known; moreover, a metal oxide exhibiting semiconductor characteristics (an oxide semiconductor) has been attracting attention as another material.

For example, Patent Document 1 discloses a technique in which a transistor is manufactured using an amorphous oxide containing In, Zn, Ga, Sn, and the like as an oxide semiconductor.

REFERENCE

Patent Document

[Patent Document 1] Japanese Published Patent Application No. 2006-165529

DISCLOSURE OF INVENTION

One object of one embodiment of the present invention is to provide a metal oxide film including a crystal part.

Another object of one embodiment of the present invention is to provide a metal oxide film having highly stable physical properties.

Another object of one embodiment of the present invention is to provide a highly reliable semiconductor device including the above metal oxide film.

Another object of one embodiment of the present invention is to provide a novel semiconductor device. Note that the descriptions of these objects do not disturb the existence of other objects. Note that in one embodiment of the present invention, there is no need to achieve all the objects. Note that other objects will be apparent from the description of the specification, the drawings, the claims, and the like and other objects can be derived from the description of the specification, the drawings, the claims, and the like.

One embodiment of the disclosed invention is a metal oxide film including a minute crystal part in which periodic atomic arrangement is not observed macroscopically or long-range order in atomic arrangement is not observed macroscopically. The metal oxide film of one embodiment of the present invention includes a region where a halo pattern indicating an amorphous state is observed in a selected-area electron diffraction pattern of the plane. On the other hand, in a nanobeam electron diffraction pattern of the cross-section, the halo pattern is not observed, and spots without directionality, which are different from spots having regularity that represents crystal parts aligned with a specific plane, are observed. Specifically, one embodiment of the disclosed invention is, for example, a metal oxide film having any of the following structures.

One embodiment of the present invention is a metal oxide film including a region where a plurality of circumferentially distributed spots are observed in a nanobeam electron diffraction pattern of a cross-section.

Another embodiment of the present invention is a metal oxide film including a region where a plurality of circumferentially distributed spots are observed in a nanobeam electron diffraction pattern of a cross-section, and a halo pattern is observed in a selected-area electron diffraction pattern of a plane.

In the above, a measurement area of the selected-area electron diffraction is preferably greater than or equal to 300 nmφ.

In the above, a measurement area of nanobeam electron diffraction is preferably greater than or equal to 5 nmφ and less than or equal to 10 nmφ. Note that irradiation with an electron beam whose beam diameter is converged to 1 nmφ can give a nanobeam electron diffraction pattern with a measurement area greater than or equal to 5 nmφ and less than or equal to 10 nmφ.

In the above, it is preferable that the nanobeam electron diffraction pattern be that of a cross-section of a sample which is thinned to greater than 10 nm and less than or equal to 50 nm.

In the above, the metal oxide film preferably includes the crystal part and the size of the crystal part is preferably less than or equal to 10 nm. Alternatively, the size of the crystal part is preferably greater than or equal to 1 nm and less than or equal to 10 nm.

One embodiment of the present invention is a metal oxide film including a crystal part which includes a region having the following features: nanobeam electron diffraction with a measurement area greater than or equal to 5 nmφ and less than or equal to 10 nmφ allows the observation of a plurality of circumferentially distributed spots from a cross-section of the metal oxide film thinned to greater than 10 nm and less than or equal to 50 nm, while spots having regularity that represents crystal parts aligned with a specific plane are observed from a cross-section of the metal oxide film thinned to less than or equal to 10 nm.

Any one of the above metal oxide films preferably contains at least indium, gallium, or zinc.

Another embodiment of the present invention is a method for forming a metal oxide film including a region where a plurality of circumferentially distributed spots are observed in a nanobeam electron diffraction pattern of a cross-section.

The metal oxide film is formed by a sputtering method at room temperature in an atmosphere containing oxygen using an oxide target.

In the above method for forming a metal oxide film, partial pressure of oxygen in the atmosphere is preferably greater than or equal to 33%.

One embodiment of the present invention can provide a metal oxide film including a crystal part.

Further, one embodiment of the present invention can provide a metal oxide film having highly stable physical properties. Furthermore, with the use of the metal oxide film in a semiconductor device, the semiconductor device can have high reliability.

BRIEF DESCRIPTION OF DRAWINGS

FIG. 22 illustrates a crystal structure of an oxide semiconductor layer used for calculation.

FIGS. 23A to 23D show calculation results for an influence of hydrogen addition on a crystal state.

BEST MODE FOR CARRYING OUT THE INVENTION

Hereinafter, embodiments of the present invention will be described in detail with reference to the accompanying drawings. Note that the present invention is not limited to the description below and it is easily understood by those skilled in the art that the modes and the aspects can be changed in various ways. Therefore, the invention should not be construed as being limited to the description in the following embodiments.

Embodiment 1

In this embodiment, a metal oxide film of one embodiment of the present invention will be described with reference to FIGS. 1A to 1D, FIGS. 2A and 2B, FIGS. 3A to 3C, FIG. 4, FIGS. 5A and 5B, FIG. 6, FIG. 7, FIGS. 15A to 15E, FIG. 16, FIGS. 17A to 17D, FIGS. 18A and 18B, FIGS. 19A to 19D, FIGS. 20A to 20C, and FIGS. 21A to 21D.

<Crystal Part in Metal Oxide Film>

The metal oxide film of this embodiment includes a minute crystal part in which periodic atomic arrangement is not observed macroscopically or long-range order in atomic arrangement is not observed macroscopically. Therefore, spots having regularity that represents a crystal state are not observed in some cases by electron diffraction when the measurement area is larger (wider) than a crystal part included therein.

<<Cross-Sectional TEM Image and Nanobeam Electron Diffraction Patterns>>

Figure 1A:
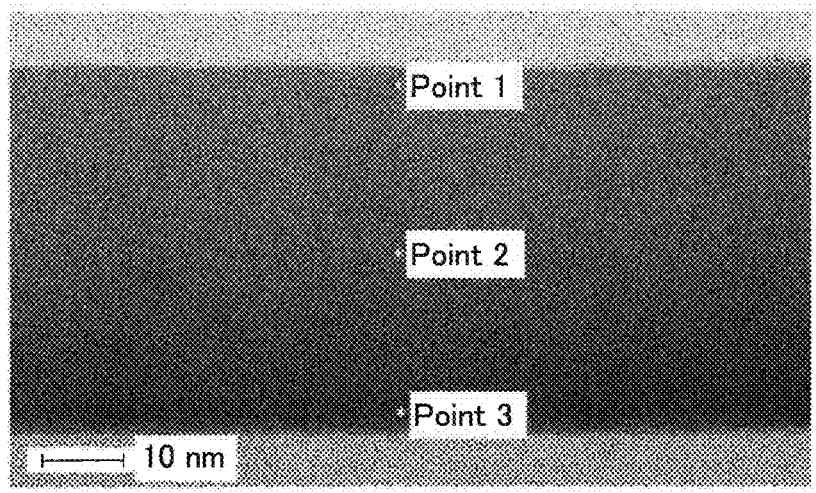
FIG. 1A is a cross-sectional TEM image of a metal oxide film of one embodiment of the present invention and FIGS. 1B to 1D are nanobeam electron diffraction patterns thereof.
Figure 1B:
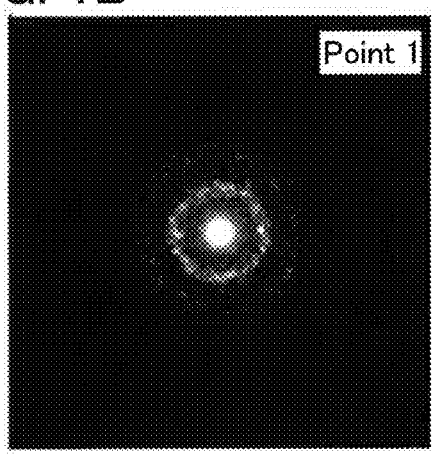
Figure 1C:
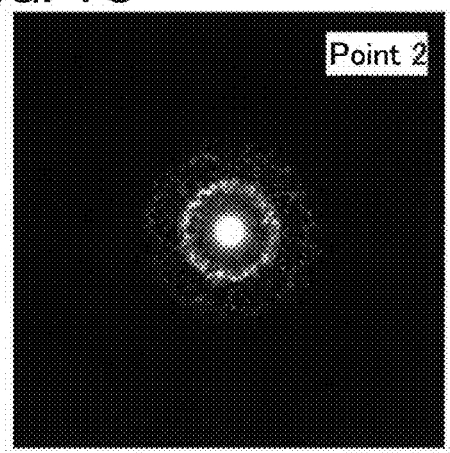
Figure 1D:
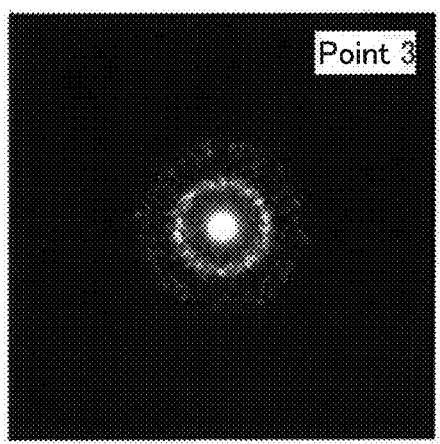

FIG. 1A is a cross-sectional transmission electron microscopy (TEM) image of the metal oxide film of this embodiment. FIGS. 1B, 1C, and 1D are electron diffraction patterns observed by nanobeam electron diffraction at points 1, 2, and 3 in FIG. 1A, respectively.

As an example of the metal oxide film, a 50-nm-thick In—Ga—Zn-based oxide film was formed over a quartz glass substrate. The metal oxide film was formed under the following conditions: an oxide target containing In, Ga, and Zn at an atomic ratio of 1:1:1 was used; an oxygen atmosphere (flow rate of 45 sccm) was used; the pressure was 0.4 Pa; the direct current (DC) power supply was 0.5 kW; and the substrate temperature was room temperature. Then, the formed metal oxide film was thinned to about 50 nm (e.g., 40 nm±10 nm) and a cross-sectional TEM image and nanobeam electron diffraction patterns were observed.

The cross-sectional TEM image of the metal oxide film was observed with a transmission electron microscope ("H-9000NAR" manufactured by Hitachi High-Technologies Corporation) at an acceleration voltage of 300 kV and at a magnification of 2000000 times. The nanobeam electron diffraction was carried out with a transmission electron microscope ("HF-2000" manufactured by Hitachi High-Technologies Corporation) at an acceleration voltage of 200 kV and a beam diameter of about 1 nmφ. Note that a measurement area of the nanobeam electron diffraction was greater than or equal to 5 nmφ and less than or equal to 10 nmφ.

As shown in FIG. 1B, in the nanobeam electron diffraction of the metal oxide film of this embodiment, circumferentially arranged spots (light spots) were observed. This means that, in the case of the metal oxide film of this embodiment, a plurality of circumferentially distributed spots are observed. It can also be said that a plurality of concentric circles are formed by a plurality of circumferentially distributed spots.

Further, also in FIG. 1C which shows the central portion of the metal oxide film in the thickness direction and in FIG. 1D which shows the vicinity of an interface with the quartz glass substrate, a plurality of circumferentially distributed spots are observed similarly to FIG. 1B. In FIG. 1C, the radius of a first circle (distance from a main spot to the circumference) is in a range from 3.88/nm to 4.93/nm, or from 0.203 nm to 0.257 nm when converted into interplanar spacing.

Apart from a halo pattern indicating an amorphous state, a plurality of spots are observed in the nanobeam electron diffraction patterns shown in FIGS. 1B to 1D. This confirms that the metal oxide film of this embodiment includes a crystal part. However, spots without directionality, which do not have regularity that represents crystal parts aligned with a specific plane, are observed in the nanobeam electron diffraction patterns shown in FIGS. 1B to 1D. Accordingly, it is assumed that the metal oxide film of this embodiment includes a plurality of crystal parts whose surface orientations are random and whose sizes are different from each other.

Figure 5A:
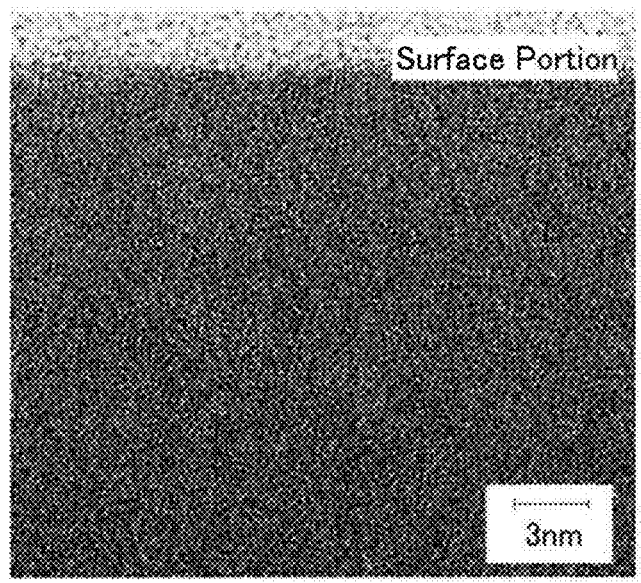
FIGS. 5A and 5B are cross-sectional TEM images of a metal oxide film of one embodiment of the present invention.
Figure 5B:
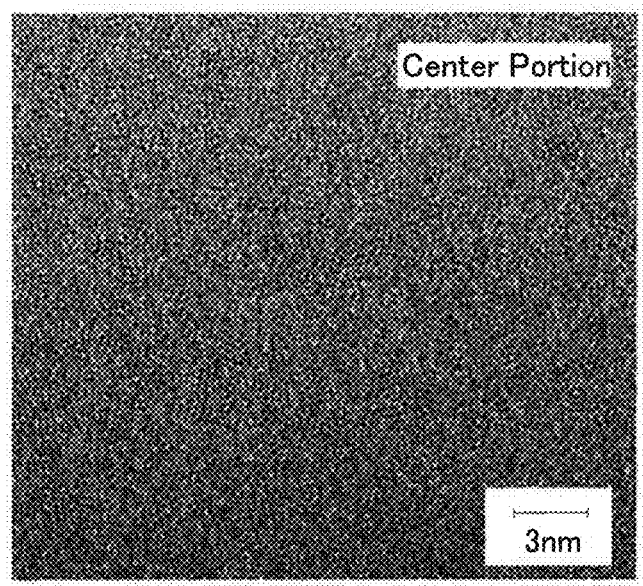

FIGS. 5A and 5B are partial enlarged views of the cross-sectional TEM image of FIG. 1A. FIG. 5A is a cross-sectional TEM image of the vicinity of the point 1 (a surface of the metal oxide film) in FIG. 1A, which is observed at an observation magnification of 8000000 times. FIG. 5B is a cross-sectional TEM image of the vicinity of the point 2 (the central portion of the metal oxide film in the thickness direction) in FIG. 1A, which is observed at an observation magnification of 8000000 times.

In the cross-sectional TEM images of the metal oxide film of this embodiment shown in FIGS. 5A and 5B, a crystal structure cannot be clearly observed.

<<Plane TEM Image and Selected-Area Electron Diffraction Pattern>>

Figure 2A:
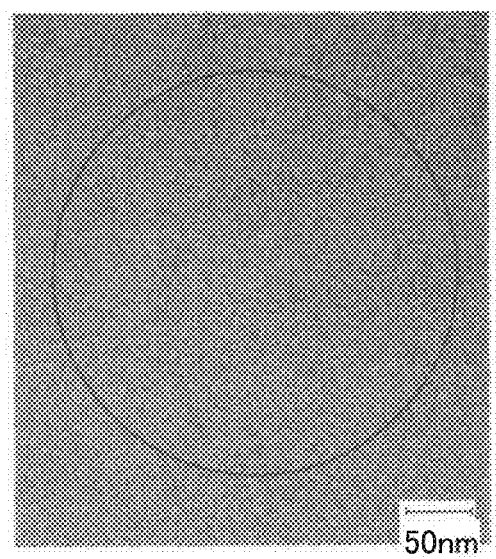
FIG. 2A is a plane TEM image of a metal oxide film of one embodiment of the present invention and FIG. 2B is a selected-area electron diffraction pattern thereof.
Figure 2B:
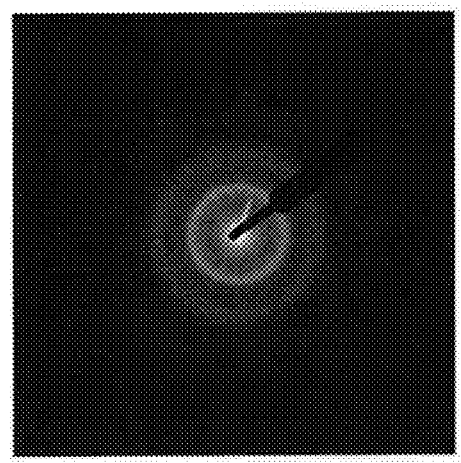

FIG. 2A is a plane TEM image of the metal oxide film of this embodiment. FIG. 2B shows an electron diffraction pattern of a region surrounded by a circle in FIG. 2A, which is observed by selected-area electron diffraction.

As an example of the metal oxide film, a 50-nm-thick In—Ga—Zn-based oxide film was formed over a quartz glass substrate. The metal oxide film was formed under the following conditions: an oxide target containing In, Ga, and Zn at an atomic ratio of 1:1:1 was used; an oxygen atmosphere (flow rate of 45 sccm) was used; the pressure was 0.4 Pa; the direct current (DC) power supply was 0.5; kW; and the substrate temperature was room temperature. Then, the formed metal oxide film was thinned to about 50 nm (e.g., 40 nm±10 nm) and a plane TEM image and a selected-area electron diffraction pattern were observed.

The images in FIGS. 2A and 2B were obtained with a transmission electron microscope ("H-9000NAR" manufactured by Hitachi High-Technologies Corporation) at an acceleration voltage of 300 kV. To obtain the image in FIG. 2A, a plane of the metal oxide film was observed at an observation magnification of 500000 times. FIG. 2B shows a diffraction result of the region in the circle in FIG. 2A obtained by selected-area electron diffraction. The pattern in FIG. 2B was obtained by electron diffraction with a selected area of 300 nmφ. In consideration of electron beam expansion (about several nanometers), a measurement area is greater than or equal to 300 nmφ.

As shown in FIG. 2B, in the case of the metal oxide film of this embodiment, the plurality of spots observed by nanobeam electron diffraction were not observed and a halo pattern was observed in an electron diffraction pattern observed by selected-area electron diffraction the measurement area of which is wider than that of the nanobeam electron diffraction. Thus, the metal oxide film of this embodiment can be regarded as a metal oxide film including a minute crystal part in which periodic atomic arrangement is not observed macroscopically (in the case where a measurement area is greater than or equal to 300 nmφ, for example) or long-range order in atomic arrangement is not observed macroscopically.

<<Conceptual Diagram of Electron Diffraction Intensity Distribution>>

Figure 3A:
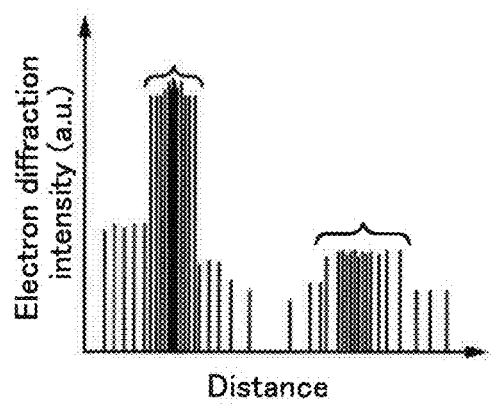
FIGS. 3A to 3C are conceptual diagrams of electron diffraction intensity distribution.
Figure 3B:
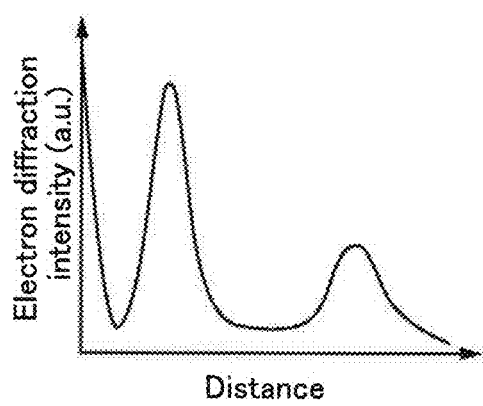
Figure 3C:
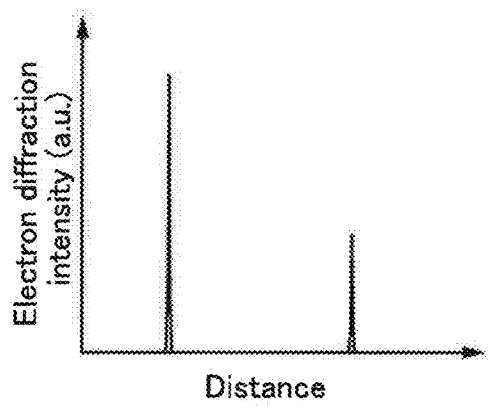

FIGS. 3A to 3C conceptually illustrate diffraction intensity distribution in the electron diffraction patterns in FIGS. 1B to 1D and FIGS. 2A and 2B. FIG. 3A is a conceptual diagram of diffraction intensity distribution in the nanobeam electron diffraction patterns in FIGS. 1B to 1D. FIG. 3B is a conceptual diagram of diffraction intensity distribution in the selected-area electron diffraction pattern in FIG. 2B. FIG. 3C is a conceptual diagram of diffraction intensity distribution in an electron diffraction pattern of an ideal polycrystalline structure.

In each of FIGS. 3A to 3C, the vertical axis represents electron diffraction intensity (arbitrary unit) and the horizontal axis represents a distance from a main spot.

In FIG. 3C for the ideal polycrystalline structure, a peak is observed at a specific distance from the main spot based on interplanar spacing (d value) of a plane with which crystal parts are aligned. In that case, in the electron diffraction pattern, a ring with a small line-width is clearly observed at the specific distance from the main spot.

On the other hand, as shown in FIGS. 1B to 1D, the circumferential region, which is formed with the plurality of spots observed in the nanobeam electron diffraction pattern of the metal oxide film of this embodiment, has a relatively large line-width. Thus, its electron beam diffraction intensity is discretely distributed and includes a plurality of zones (peak zones) in which peaks are distributed, as shown in FIG. 3A. Note that a small number of spots are observed between the plurality of the circumferentially arranged regions in the nanobeam electron diffraction pattern. This means that, as shown in FIG. 3A, diffraction peaks exist between two peak zones.

On the other hand, the electron beam diffraction intensity distribution in the selected-area electron diffraction pattern of the metal oxide film of this embodiment is continuous as shown in FIG. 3B. Since FIG. 3B can approximate to a result obtained by observing the electron beam diffraction intensity distribution shown in FIG. 3A in a wide area, it can be considered that the peak zone in FIG. 3A is integrated and the continuous intensity distribution is obtained.

FIGS. 3A to 3C indicate that the metal oxide film of this embodiment includes a plurality of crystal parts whose surface orientations are random and whose sizes are different from each other, and the crystal parts are so minute that spots are not observed in the selected-area electron diffraction patterns.

The metal oxide film which gives a plurality of spots in the nanobeam electron diffraction pattern as shown in FIGS. 1B to 1D is thinned to about 50 nm. Further, since the beam diameter of the electron beam is converged to 1 nmφ, the measurement area is greater than or equal to 5 nm and less than or equal to 10 nm. Accordingly, it is assumed that the size of the crystal part included in the metal oxide film of this embodiment is at least less than or equal to 50 nm, for example, less than or equal to 10 nm or less than or equal to 5 nm.

<<Nanobeam Electron Diffraction Pattern of Extremely Thin Sample>>

In the case where the size of the crystal part included in the metal oxide film of this embodiment is less than or equal to 10 nm or less than or equal to 5 nm, a measurement area in the depth direction is larger than the size of the crystal part in the sample in which the metal oxide film is thinned to about 50 nm; as a result, a plurality of crystal parts are observed in the measurement area, in some cases. Thus, a metal oxide film thinned to less than or equal to 10 nm was formed, and its cross section was observed by nanobeam electron diffraction.

A method for forming the sample is as follows. A 50-nm-thick In—Ga—Zn-based oxide film was formed over a quartz glass substrate. The film was formed under the following conditions: an oxide target containing In, Ga, and Zn at an atomic ratio of 1:1:1 was used; an oxygen atmosphere (flow rate of 45 sccm) was used; the pressure was 0.4 Pa; the direct current (DC) power supply was 0.5 kW; and the substrate temperature was room temperature. After the metal oxide film was formed, first heat treatment was performed at 450° C. in a nitrogen atmosphere for one hour and second heat treatment was performed at 450° C. in an atmosphere containing nitrogen and oxygen for one hour.

Figure 16:
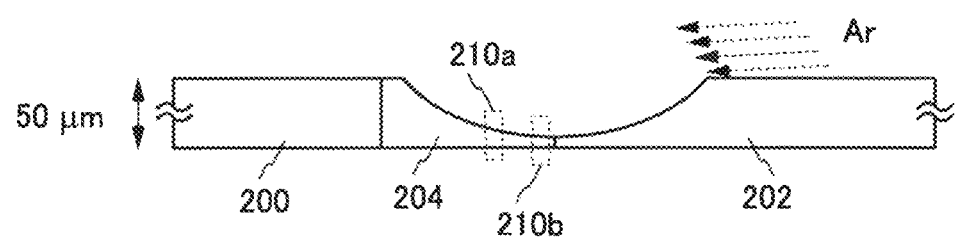
FIG. 16 is a conceptual diagram illustrating a method for thinning a sample by an ion milling method.

The metal oxide film on which the second heat treatment was performed was further thinned by an ion milling method using Ar ions. First, the quartz glass substrate over which the metal oxide film was formed was attached to a dummy substrate for reinforcement. Then, the film was thinned to about 50 μm by cutting and polishing. After that, as illustrated in FIG. 16, a metal oxide film 204 provided to a quartz glass substrate 200 and a dummy substrate 202 were irradiated with argon ions at a steep angle (about 3°) so that ion milling was performed to form a region 210a which was thinned to about 50 nm (40 nm±10 nm) and a region 210b which was thinned to less than or equal to 10 nm, for example, 5 nm to 10 nm. Then, the cross section of each region was observed.

Figure 15A:
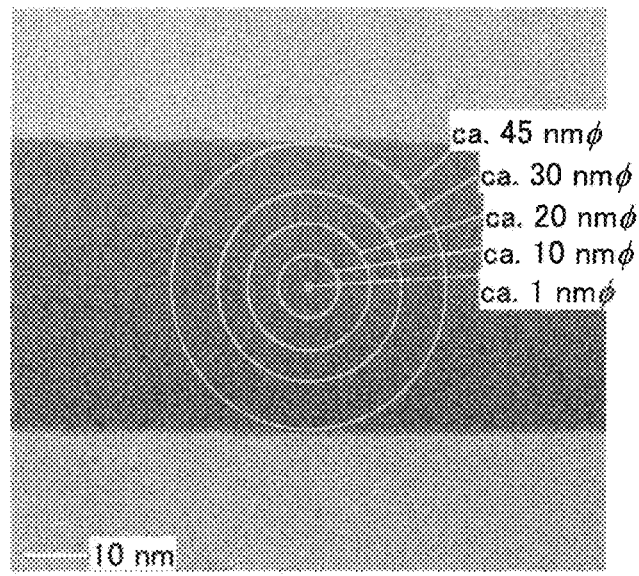
FIG. 15A is a cross-sectional TEM image of a metal oxide film of one embodiment of the present invention and FIGS. 15B to 15E are nanobeam electron diffraction patterns thereof.
Figure 15B:
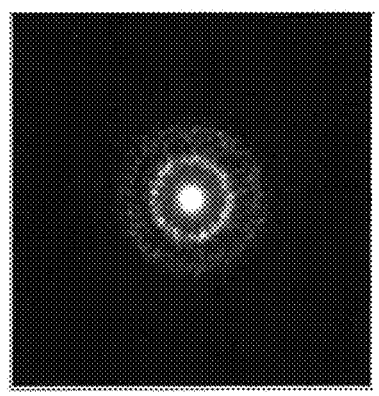
Figure 15C:
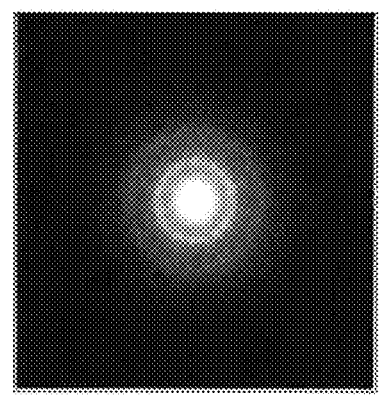
Figure 15D:
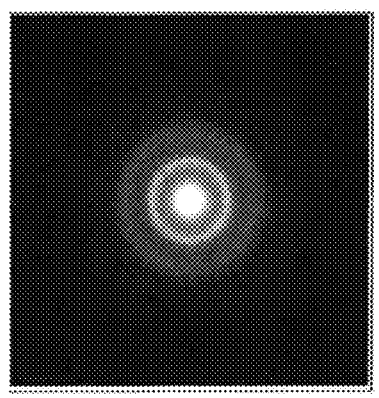
Figure 15E:
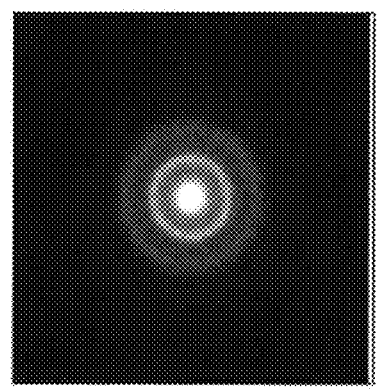

FIG. 15A is a cross-sectional TEM image of a sample thinned to about 50 nm, which corresponds to the region 210a. FIGS. 15B to 15E show electron diffraction patterns observed by nanobeam electron diffraction of the cross section shown in FIG. 15A. FIG. 15B shows an electron diffraction pattern observed with the use of an electron beam whose beam diameter is converged to 1 nmφ. FIG. 15C shows an electron diffraction pattern observed with the use of an electron beam whose beam diameter is converged to 10 nmφ FIG. 15D shows an electron diffraction pattern observed with the use of an electron beam whose beam diameter is converged to 20 nm . FIG. 15E shows an electron diffraction pattern observed with the use of an electron beam whose beam diameter is converged to 30 nmφ.

As shown in FIG. 15B, a plurality of circumferentially distributed spots (light spots), which are similar to those in FIGS. 1B to 1D, are observed also in the metal oxide film on which heat treatment is performed. Further, as shown in FIGS. 15C to 15E, when the beam diameter of an electron beam is increased to observe a wider measurement area, the spots are gradually blurred.

FIGS. 17A to 17D show nanobeam electron diffraction patterns at four given points in a sample thinned to less than or equal to 10 nm, which corresponds to the region 210b. The nanobeam electron diffraction patterns are observed with the use of an electron beam whose beam diameter is converged to 1 nmφ.

Figure 17A:
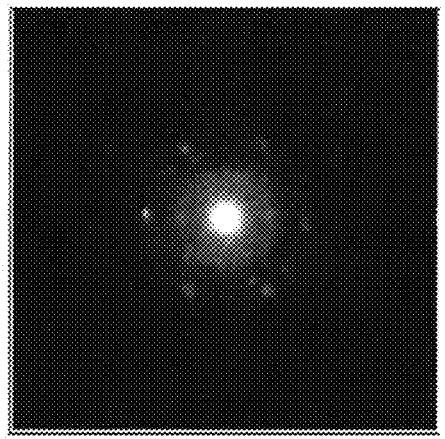
FIGS. 17A to 17D are each a nanobeam electron diffraction pattern of a metal oxide film of one embodiment of the present invention.
Figure 17B:
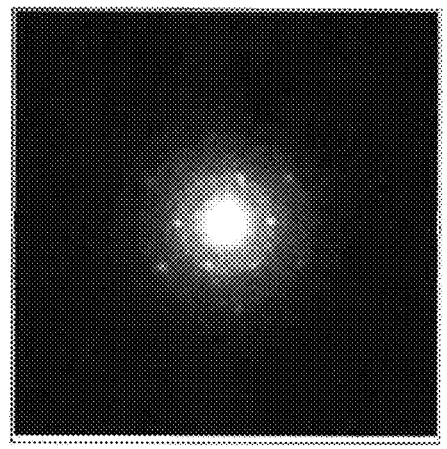
Figure 17C:
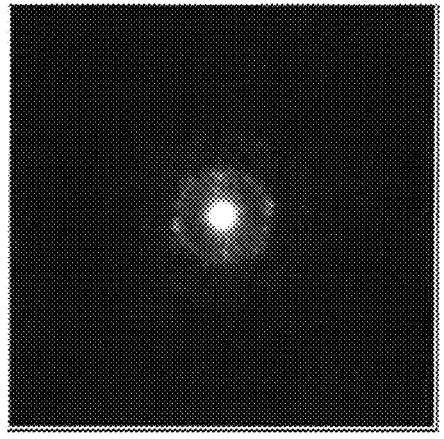
Figure 17D:
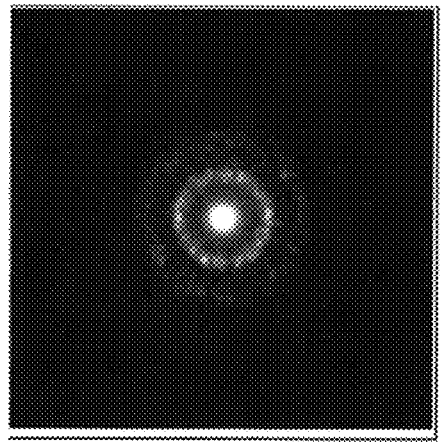

In FIGS. 17A and 17B, spots having regularity that represents crystal parts aligned with a specific plane are observed. This indicates that the metal oxide film of this embodiment undoubtedly includes a crystal part. In FIGS. 17C and 17D, on the other hand, a plurality of circumferentially distributed spots (light spots) are observed.

As described above, the size of the crystal part included in the metal oxide film of this embodiment is minute and is at least less than or equal to 50 nm, for example, less than or equal to 10 nm or less than or equal to 5 nm. Thus, in the case where a sample is thinned to less than or equal to 10 nm and the diameter of an electron beam is converged to 1 nmφ to make a measurement area smaller than the size of one crystal part, for example, spots having regularity that represents crystal parts aligned with a specific plane can be observed, depending the measured regions. In the case where a plurality of crystal parts are included in the observed region, an electron beam transmitted through a crystal part further irradiates another crystal part located in the depth direction, which would result in the observation of a plurality of nanobeam electron diffraction patterns.

<<Nanobeam Electron Diffraction Pattern of Quartz Substrate>>

Figure 4:
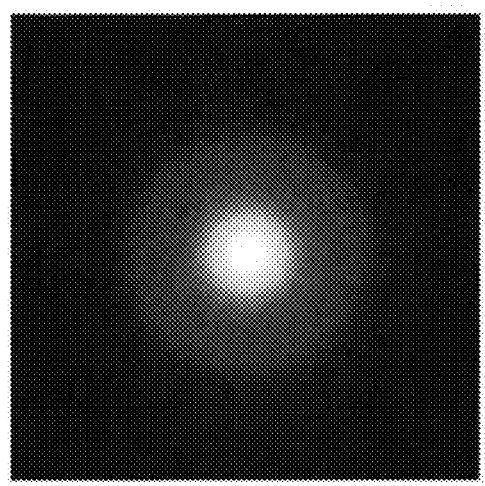
FIG. 4 is a nanobeam electron diffraction pattern of a quartz glass substrate.

FIG. 4 shows a nanobeam electron diffraction pattern of a quartz glass substrate. The measurement conditions are the same as those for the oxide semiconductor film shown in FIGS. 1B to 1D.

As shown in FIG. 4, a halo pattern in which a specific spot is not given by diffraction and whose luminance is gradually changed form a main spot is observed in the case of a quartz glass substrate having an amorphous structure. Thus, circumferentially arranged spots like those observed in the metal oxide film of this embodiment are not observed in a film having an amorphous structure even when electron diffraction is performed on a minute region. This confirms that the circumferentially arranged spots observed in FIGS. 1B to 1D are peculiar to the metal oxide film of this embodiment.

<<Electron Diffraction Pattern after Continuous Irradiation with Nanobeam>>

Figure 8:
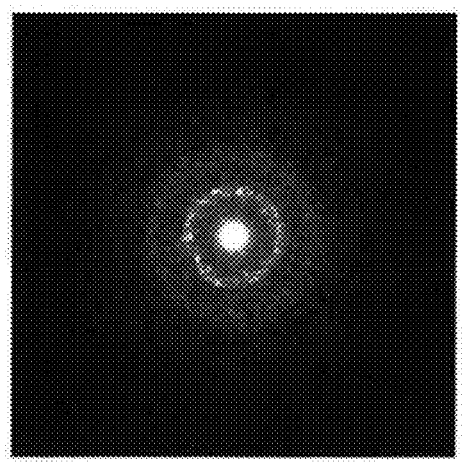
FIG. 8 is a nanobeam electron diffraction pattern of a metal oxide film of one embodiment of the present invention.

FIG. 8 shows an electron diffraction pattern observed after the point 2 in FIG. 1A is irradiated with an electron beam whose beam diameter is converged to about 1 nmφ for one minute.

Similarly to the electron diffraction pattern shown in FIG. 1C, a plurality of circumferentially distributed spots are observed in the electron diffraction pattern shown in FIG. 8, and there is no significant difference between the electron diffraction patterns in FIG. 1C and FIG. 8. This means that the crystal part identified by FIG. 1C is formed when the metal oxide film of this embodiment is formed and is not resulted from the irradiation of the converged electron beam.

<<Analysis by X-Ray Diffraction>>

Figure 6:
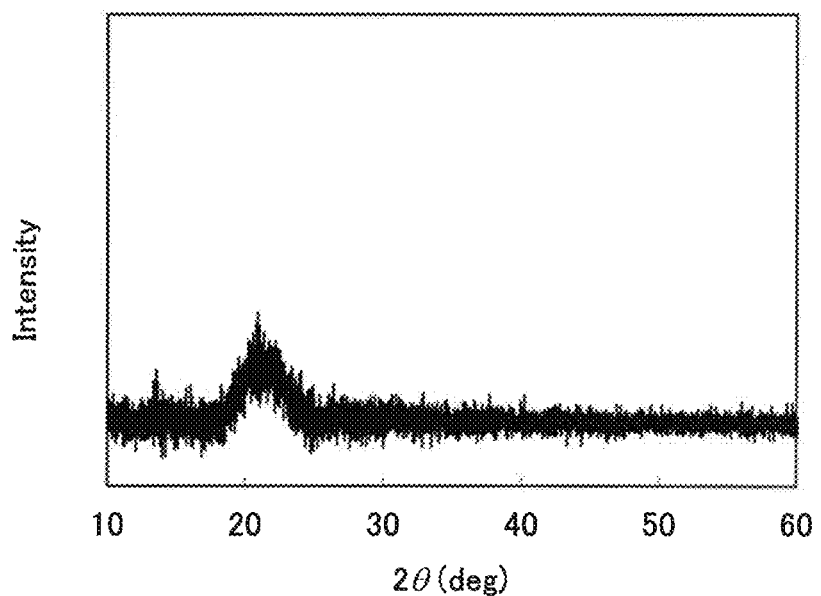
FIG. 6 shows a result of X-ray diffraction analysis of a metal oxide film of one embodiment of the present invention.

The sample of the metal oxide film of this embodiment formed over a quartz glass substrate, which is used for FIGS. 1A to 1D and FIGS. 2A and 2B, was analyzed by X-ray diffraction (XRD). FIG. 6 shows an XRD spectrum measured by an out-of-plane method.

In FIG. 6, the vertical axis represents the X-ray diffraction intensity (arbitrary unit) and the horizontal axis represents the diffraction angle 2θ (degree). Note that the XRD spectra were measured with an X-ray diffractometer, D8 ADVANCE manufactured by Bruker AXS.

As shown in FIG. 6, a peak corresponding to quartz appears at around 2θ=20° to 23°; however, a peak corresponding to the crystal part included in the metal oxide film cannot be found.

The result in FIG. 6 indicates that the crystal part included in the metal oxide film of this embodiment is minute.

According to the above results, it can be assumed that the metal oxide film of this embodiment is a film in which crystal parts whose surface orientations are random are cohered.

In addition, it is assumed that the size of a crystal part included in the metal oxide film of this embodiment is less than or equal to 10 nm or less than or equal to 5 nm, for example. The metal oxide film of this embodiment includes a crystal part (nanocrystal (nc)) whose size is greater than or equal to 1 nm and less than or equal to 10 nm, for example.

<Method for Forming Metal Oxide Film>

A method for forming the metal oxide film of this embodiment is described below. As described above, the metal oxide film of this embodiment is formed by a sputtering method at room temperature in an atmosphere containing oxygen. With the use of the atmosphere containing oxygen, oxygen vacancies in the metal oxide film can be reduced and a film including a crystal part can be formed.

<<Reduction in Oxygen Vacancy>>

A reduction of oxygen vacancies in the metal oxide film of this embodiment allows the formation of a film having stable physical properties. In particular, in the case where a semiconductor device is formed using an oxide semiconductor film as the metal oxide film of this embodiment, oxygen vacancies in the oxide semiconductor film cause carriers to be generated; as a result, the electric characteristics of the semiconductor device vary. Thus, a semiconductor device formed using an oxide semiconductor film in which oxygen vacancies are reduced can be highly reliable.

Note that it is preferable to increase the oxygen partial pressure in the deposition atmosphere because the oxygen vacancies in the metal oxide film of this embodiment can be further reduced. For example, the oxygen partial pressure in the deposition atmosphere is preferably greater than or equal to 33%.

Figure 7:
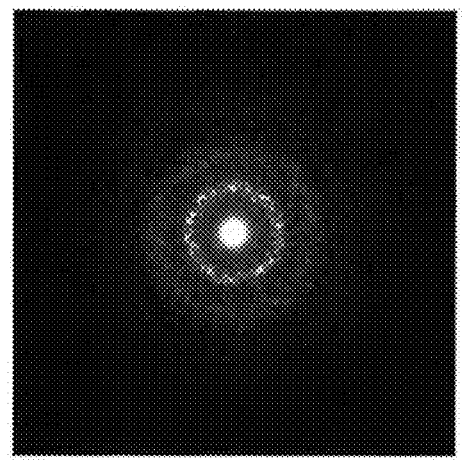
FIG. 7 is a nanobeam electron diffraction pattern of a metal oxide film of one embodiment of the present invention.

FIG. 7 shows a nanobeam electron diffraction pattern of the metal oxide film of this embodiment which was formed at an oxygen partial pressure of 33%. The metal oxide film of this embodiment shown in FIG. 7 was formed under conditions similar to those of the metal oxide film shown in FIGS. 1A to 1D except that a mixture of argon and oxygen (flow rate of Ar and $O_2$ are 30 sccm and 15 sccm, respectively) was used as the deposition atmosphere. The nanobeam electron diffraction was carried out in a manner similar to that explained for FIGS. 1B to 1D.

In the metal oxide film of this embodiment which is formed at an oxygen partial pressure of 33%, circumferentially arranged spots are also observed in the nanobeam electron diffraction pattern shown in FIG. 7. This confirms that a metal oxide film including a crystal part is formed.

<<Deposition by Sputtering Method>>

An oxide target that can be used for forming the metal oxide film of this embodiment is not limited to an In—Ga—Zn-based oxide; for example, an In-M-Zn-based oxide (M is Al, Ti, Ga, Y, Zr, La, Ce, Nd, or Hf) can be used.

The metal oxide film of this embodiment, which includes a crystal part, is preferably formed using a sputtering target including a polycrystalline oxide containing a plurality of crystal grains. The reason is as follows. In the case where the sputtering target contains a plurality of crystal grains and there are interfaces that are likely to cause cleavage of the crystal grains because of weak bondings between the plurality of crystal grains, the crystal grains are cleaved along the interfaces when ions collide with the sputtering target, whereby flat plate-like sputtered particles can be obtained in some cases. The obtained flat plate-like sputtered particles are deposited on a substrate; accordingly, a metal oxide film including a nanocrystal region is formed in some cases. Note that the above mechanism to form the metal oxide film of this embodiment is one consideration.

The above-described metal oxide film of this embodiment includes a plurality of crystal parts whose surface orientations are random and whose sizes are different from each other, and the crystal parts are so minute that spots are not observed in the selected-area electron diffraction pattern.

Further, the metal oxide film of this embodiment includes a region having a crystal part and has stable physical properties. Accordingly, with the use of the metal oxide film of this embodiment in a semiconductor device, the semiconductor device can have high reliability.

Comparative Example

In this comparative example, the crystallinity of a metal oxide film formed by a liquid phase method will be described with reference to drawings.

A method for forming the metal oxide film of this comparative example will be described below.

First, $In_2O_3$ (5 wt %), $Ga_2O_3$ (3 wt %), ZnO (5 wt %), and a coating agent were mixed so that the mixture contains In, Ga, and Zn at a composition ratio of 1:1:1, and the mixture was applied to a glass substrate by spin coating. The conditions for the spin coating were as follows: a spinner was used; and the spinning rate was changed stepwise from 900 rpm to 2000 rpm.

After that, first heat treatment was performed at 150° C. in an air atmosphere for two minutes using a hot plate.

Subsequently, second heat treatment was performed at 450° C. in an air atmosphere for one hour. The bonding state of the metal oxide film (formed by a liquid phase method) of this comparative example subjected to the second heat treatment, and the bonding state of the metal oxide film (formed by a sputtering method) of this embodiment formed under the same conditions as those of the metal oxide film shown in FIG. 7 were analyzed by X-ray photoelectron spectroscopy (XPS). FIGS. 24A to 24D show the analysis results.

The XPS analysis was carried out with Quantera SXM manufactured by Physical Electronics, Inc. as an analysis apparatus. FIGS. 24A to 24D show the spectra in the regions corresponding to 3d(5/2) orbital of In (see FIG. 24A), 3d orbital of Ga (see FIG. 24B), 3p orbital of Zn (see FIG. 24C), and 1s orbital of O (see FIG. 24D) of each of the metal oxide films. Solid lines in FIGS. 24A to 24D corresponds to the analysis results of the In—Ga—Zn oxide film of this comparative example, which was formed by a liquid phase method. Dashed lines in FIGS. 24A to 24D corresponds to the analysis results of the In—Ga—Zn oxide film of this embodiment, which was formed by a sputtering method (sputtering).

In FIGS. 24A to 24D, although there is a slight difference between bond energies, the metal oxide film of this comparative example, which was formed by a liquid phase method, and the metal oxide film of this embodiment, which was formed by a sputtering method, have substantially the same spectral shapes. Thus, the metal oxide film of this comparative example, which was formed by a liquid phase method, was identified as an In—Ga—Zn oxide film.

Next, the formed samples of the comparative example were analyzed by XRD. FIGS. 19A to 19D show the results of the analysis by an out-of-plane method.

In the XRD analysis were used the samples of the In—Ga—Zn oxide film which were subjected to the second heat treatment at 350° C., 450° C., or 550° C. in an air atmosphere for one hour after the first heat treatment.

In FIGS. 19A to 19D, the vertical axis represents the X-ray diffraction intensity (arbitrary unit) and the horizontal axis represents the diffraction angle 2θ (degree). The XRD measurements were carried out with an X-ray diffractometer, D8 ADVANCE manufactured by Bruker AXS.

Figure 19A:
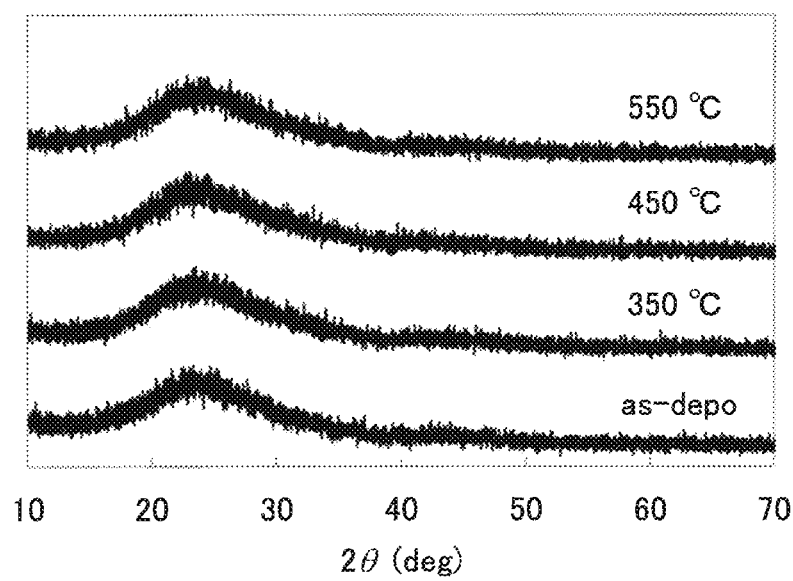
FIGS. 19A to 19D each show results of X-ray diffraction analysis of samples prepared by a liquid phase method.
Figure 19B:
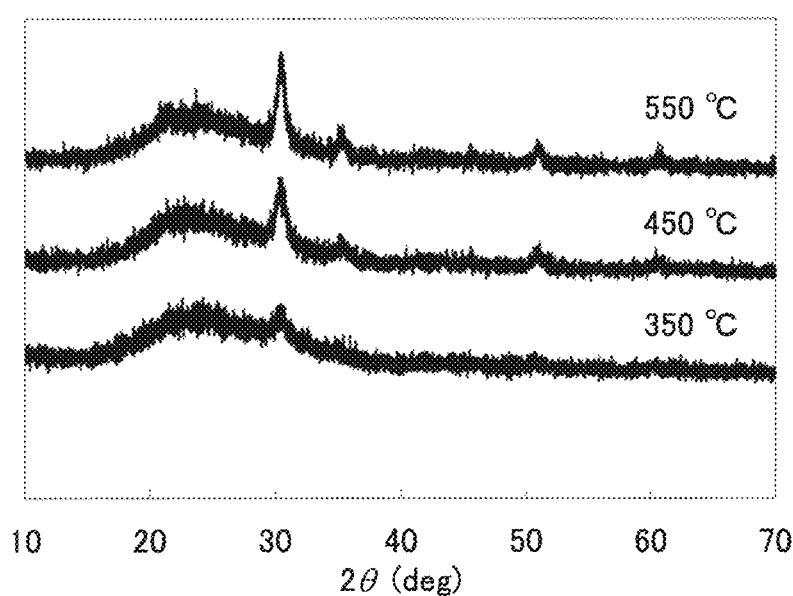
Figure 19C:
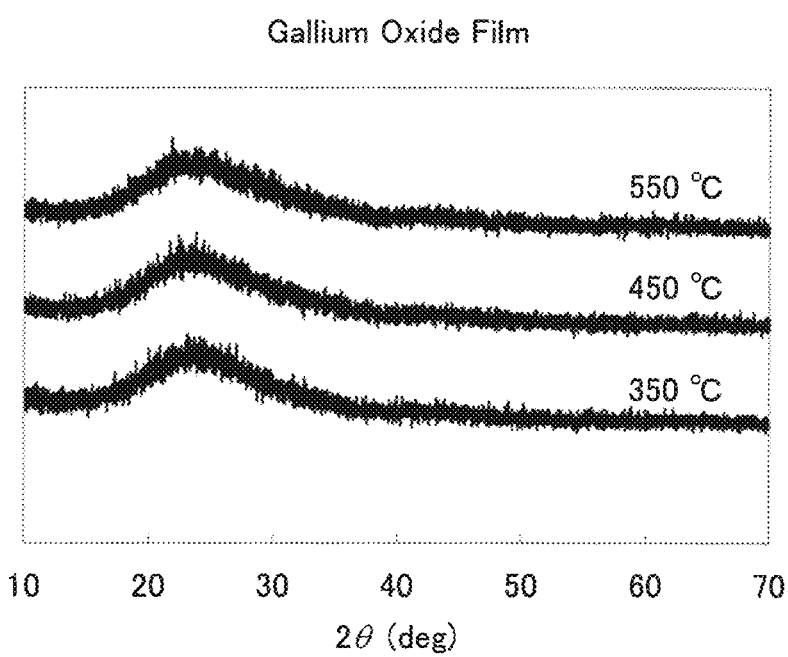
Figure 19D:
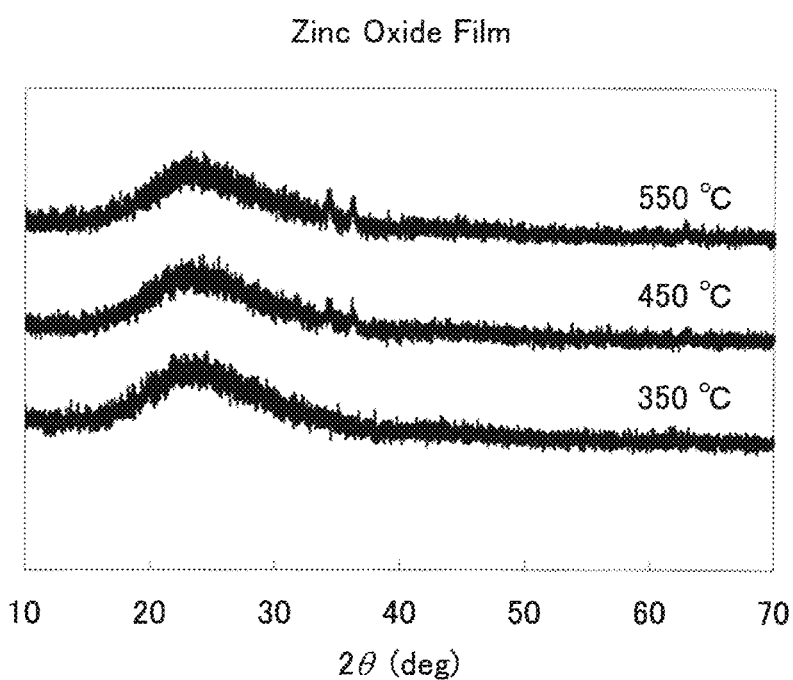

FIG. 19A shows the measurement results of the samples of this comparative example formed by a liquid phase method. The XRD pattern of the sample which is not subjected to the heat treatment is the pattern denoted by "as-depo". Note that FIGS. 19B to 19D show the measurement results of indium oxide films, gallium oxide films, and zinc oxide films which are formed by a liquid phase method and subjected to heat treatment at 350° C., 450° C., or 550° C. in an air atmosphere for one hour.

As shown in FIGS. 19A to 19D, peaks corresponding to $In_2O_3$ crystalline peaks are found in the XRD pattern of the indium oxide films after the heat treatment. In addition, peaks corresponding to ZnO crystalline peaks are found in the XRD pattern of the zinc oxide films after the heat treatment. In the samples of this comparative example subjected to heat treatment at any of the temperature, on the other hand, a crystalline peak is not found unlike in the indium oxide films and the zinc oxide films.

Then, the film density of each of the samples which were subjected to the second heat treatment at 450° C. in an air atmosphere for one hour was measured by X-ray reflectometry (XRR).

Note that XRR is a measurement method for measuring the density of a deposited thin film, in which X-rays are incident on a measurement sample to measure critical angles and changes in amplitude waveforms of the incident X-rays and theoretical analysis is performed using the critical angles and the amplitude waveforms.

Table 1 shows the measured film density.

TABLE 1

| Sample | Crystallinity | Film Density (g/cm³) | |
|---|---|---|---|
| | | Observed | Theoretical |
| In—Ga—Zn Oxide Film (In:Ga:Zn = 1:1:1) | No peak | 3.27 | 6.35 |
| Indium Oxide Film | Peak assignable to $In_2O_3$ | 4.26 | 7.12 |
| Gallium Oxide Film | No peak | 3.61 | 5.94 |
| Zinc Oxide Film | Peak assignable to ZnO | 4.06 | 5.67 |

As shown in Table 1, the films formed by a liquid phase method have extremely low density as compared with the theoretical values calculated on the basis of their single crystal structures. Note that it is difficult to measure the film density with high accuracy because a film formed by a liquid phase method has large roughness.

Next, the concentrations of impurities contained in the metal oxide film of this comparative example and the metal oxide film of this embodiment were measured by SIMS.

Figure 18A:
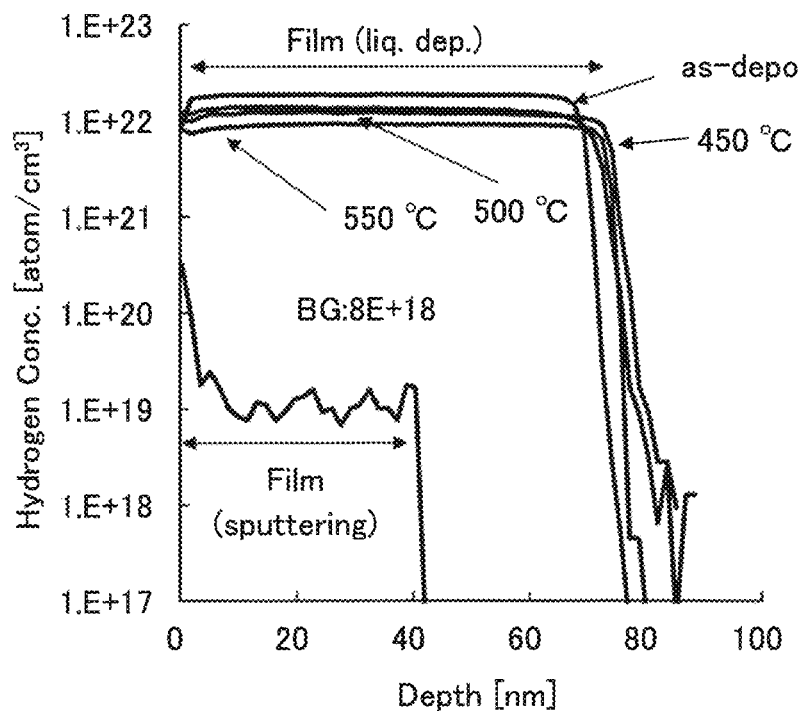
FIGS. 18A and 18B show SIMS analysis results of metal oxide films in a comparative example and one embodiment.
Figure 18B:
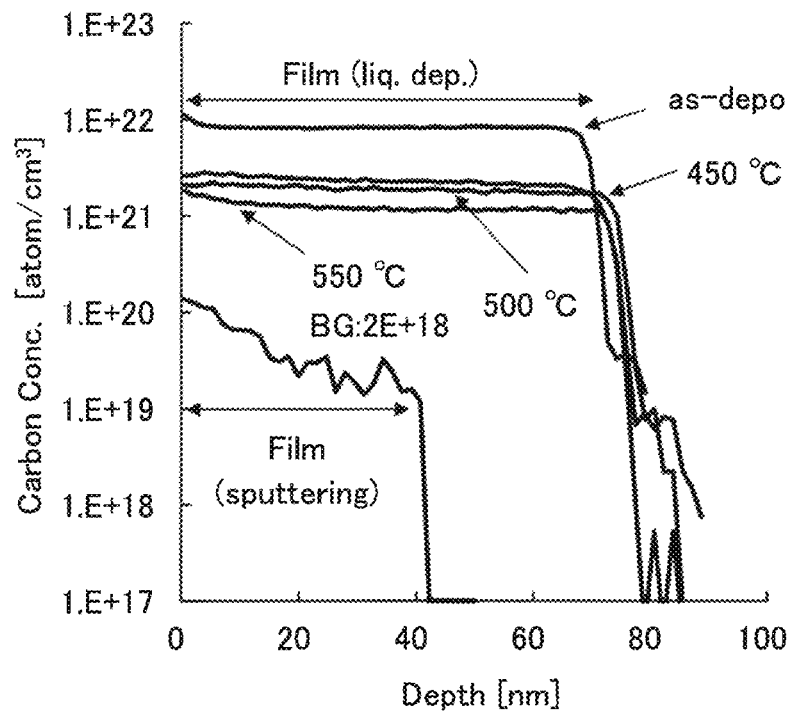

FIG. 18A shows concentration profiles of hydrogen (1H) in the metal oxide films of the comparative example and the metal oxide film of this embodiment. FIG. 18B shows concentration profiles of carbon (12C) in the metal oxide films of the 20 comparative example and the metal oxide film of this embodiment. In FIGS. 18A and 18B, the horizontal axis represents a depth (nm) and the vertical axis represents the concentration of hydrogen or carbon (atoms/cm³).

Samples formed by a liquid phase method under the conditions similar to those described above were used as the metal oxide films of the comparative example for FIGS. 18A and 18B. Note that filtration using a membrane filter (0.2 μm) was performed on the material before spin coating. In addition, the second heat treatment was performed at 450° C., 500° C., or 550° C. in an air atmosphere for one hour. The other conditions were the same as those of the above metal oxide films formed by a liquid phase method. A sample formed by a sputtering method under the same conditions as those of the metal oxide film shown in FIG. 7 was used for the metal oxide film of this embodiment.

As shown in FIGS. 18A and 18B, large amounts of hydrogen and carbon uniformly exist in the metal oxide films of the comparative example as compared with the metal oxide film of this embodiment.

The carbon concentration of the metal oxide film of this embodiment shown in FIG. 18B is gradually decreased from its surface to the inside the film. This suggests that carbon in the metal oxide film of this embodiment is mainly due to the surface contamination.

In contrast, the metal oxide films formed under any conditions of the comparative example uniformly contain hydrogen at a density as high as $1\times10^{22}$ (atoms/cm³) or more and carbon at a density as high as $4\times10^{21}$ (atoms/cm³) or more. It is assumed that carbon in the metal oxide films of the comparative example is due to an organic acid salt which is a raw material of a spin coating material.

Figure 20A:
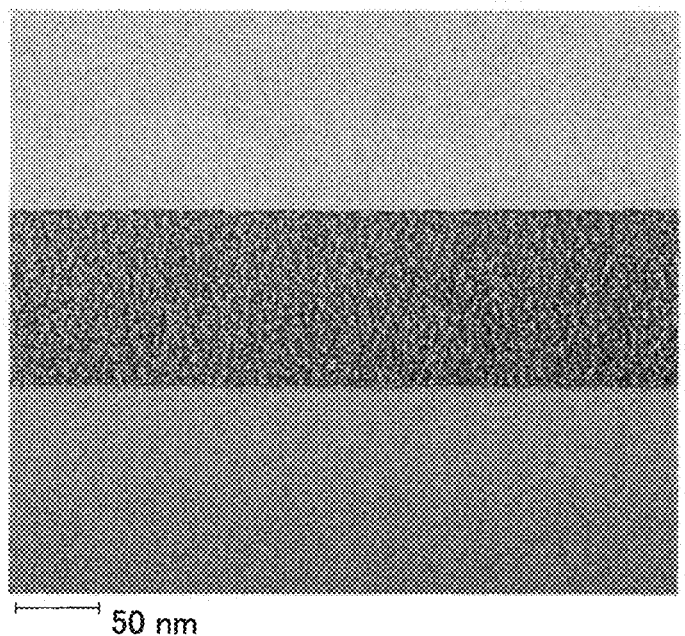
FIGS. 20A to 20C are cross-sectional TEM images of a sample in a comparative example.
Figure 20B:
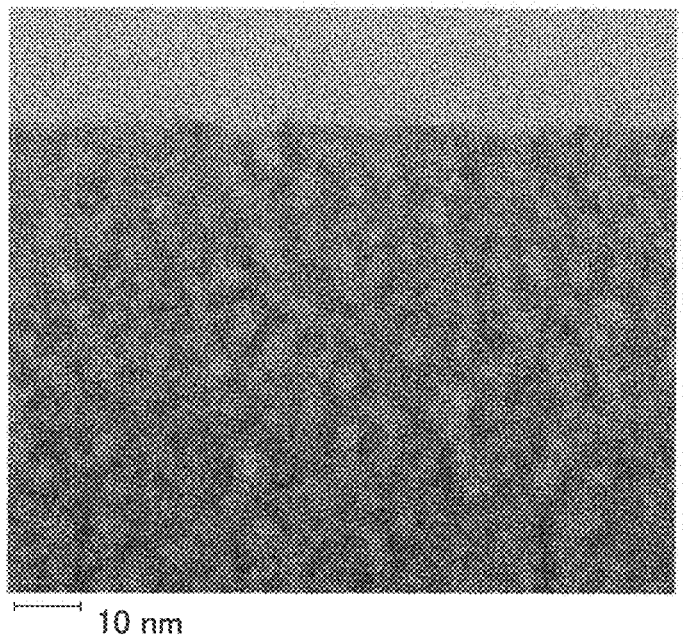
Figure 20C:
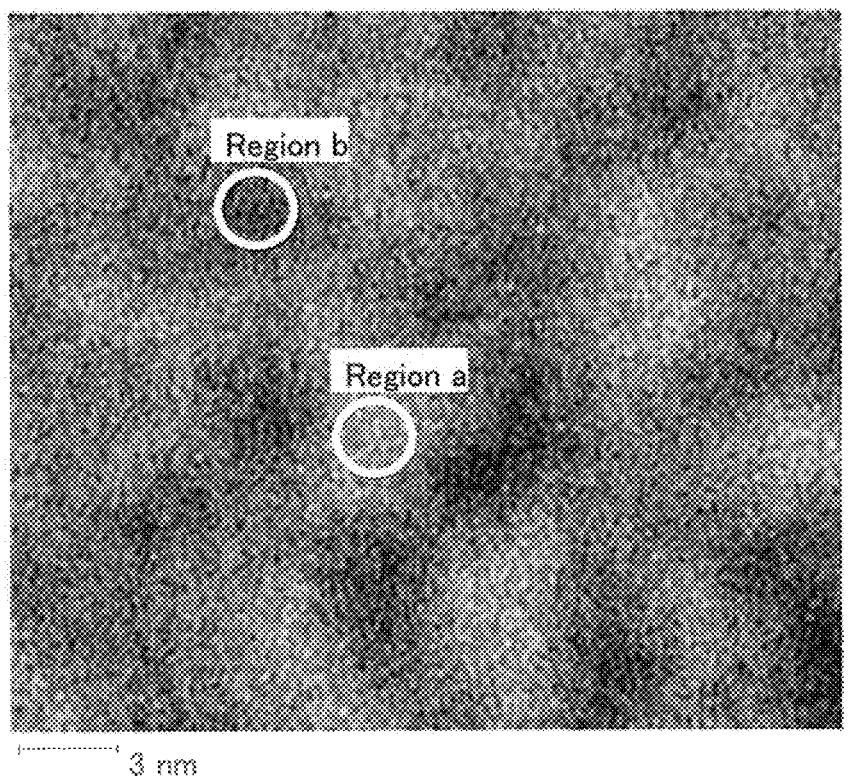

Next, cross-sectional TEM images of the sample of this comparative example, which was subjected to the second heat treatment at 450° C. in an air atmosphere for one hour, are shown in FIGS. 20A to 20C. The cross section was observed with a transmission electron microscope ("H-9000NAR" manufactured by Hitachi High-Technologies Corporation) at an acceleration voltage of 300 kV. FIG. 20A is a cross-sectional image at a magnification of 500000. FIG. 20B is a cross-sectional image at a magnification of 2000000. FIG. 20C is a cross-sectional observation image at a magnification of 8000000.

As seen in FIGS. 20A and 20B, a large part of the sample of this comparative example formed by a liquid phase method is occupied by an amorphous region. In addition, a shade of gray (variation in brightness) due to the difference in film density can be seen.

In a region a in the cross-sectional TEM image in FIG. 20C, the brightness is high, which means that the region a has low film density. In a region b in the cross-sectional TEM image in FIG. 20C, the brightness is low, which means that the region b has high density.

Figure 21A:
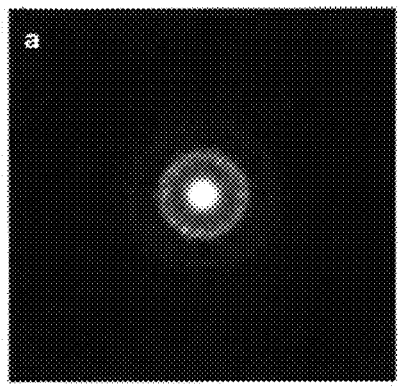
FIGS. 21A to 21C are nanobeam electron diffraction patterns of a sample in a comparative example and FIG. 21D is a nanobeam electron diffraction pattern of a metal oxide film of one embodiment of the present invention.
Figure 21B:
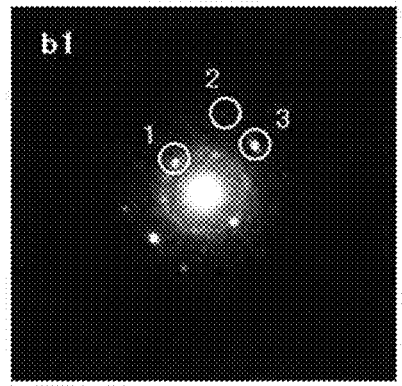
Figure 21C:
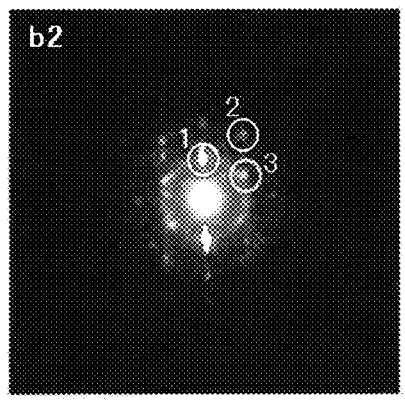

The regions a and b in FIG. 20C were observed by nanobeam electron diffraction. FIGS. 21A to 21C show nanobeam electron diffraction patterns.

The nanobeam electron diffraction was carried out with a transmission electron microscope ("HF-2000" manufactured by Hitachi High-Technologies Corporation) at an acceleration voltage of 200 kV and a beam diameter of about 1 nmφ. FIG. 21A shows a nanobeam electron diffraction pattern of the region a in FIG. 20C. FIGS. 21B and 21C show nanobeam electron diffraction patterns of two different portions (denoted by b1 and b2) in the region b in FIG. 20C.

Figure 21D:
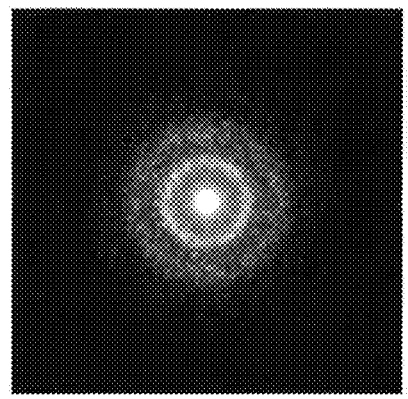
Figure 24A:
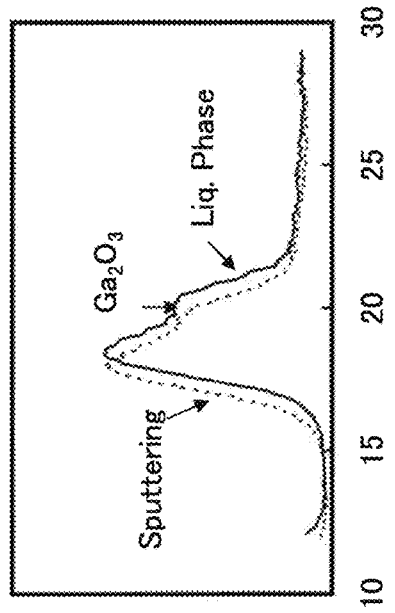
FIGS. 24A to 24D show measurement results of bond energy in a metal oxide film of one embodiment of the present invention and a sample in a comparative example by XPS.
Figure 24B:
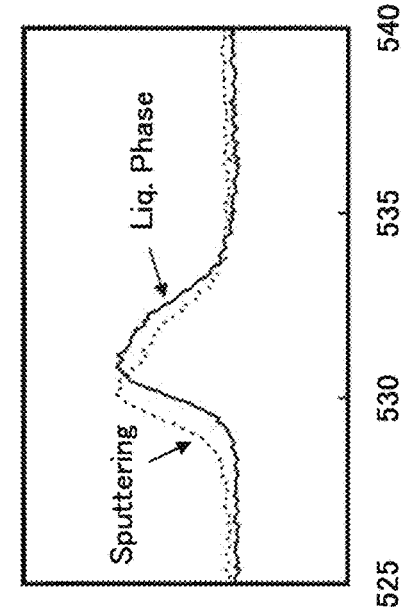
Figure 24C:
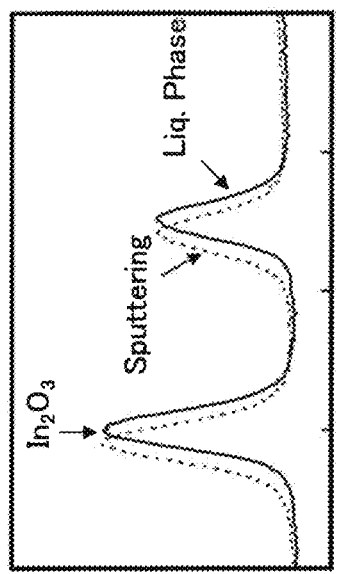
Figure 24D:
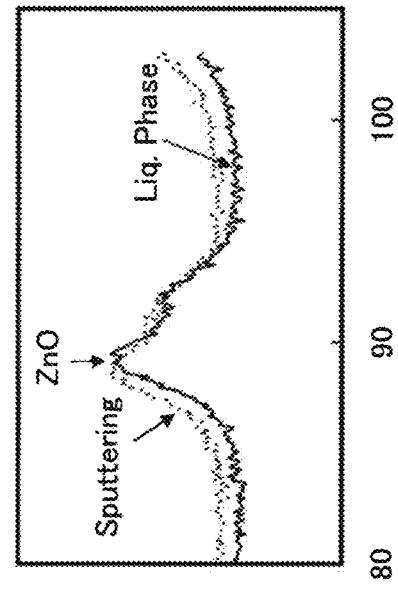

FIG. 21D shows a nanobeam electron diffraction pattern of the metal oxide film of one embodiment of the present invention, which was formed and observed under the same conditions as those of the metal oxide film shown in FIG. 7.

As shown in FIGS. 21A to 21C, a pattern, which is different from the circumferentially arranged spots (light spots) observed in the metal oxide film of one embodiment of the present invention shown in FIG. 21D, was observed in each region in the metal oxide film of this comparative example formed by a liquid phase method.

The nanobeam electron diffraction pattern of the region a shown in FIG. 21A is similar to a halo pattern indicating an amorphous state. The presence of a region having such low crystallinity may be due to the low density and the high impurity concentration of the film.

As shown in FIGS. 21B and 21C, spots (denoted by 1 to 3 in FIGS. 21B and 21C) having regularity that represents crystal parts aligned with a specific plane are observed in the nanobeam electron diffraction patterns of the region b. The analysis results of the diffraction patterns of these spots are shown in Table 2 below.

TABLE 2

| Region | Spot | h | k | l | d value (nm) Theoretical | d value (nm) Observed |
|---|---|---|---|---|---|---|
| b1 | 1 | 1 | 0 | 4 | 0.261 | 0.263 |
|  | 2 | 2 | 2 | 4 | 0.139 | 0.138 |
|  | 3 | 1 | 2 | 0 | 0.165 | 0.165 |
| b2 | 1 | 0 | 0 | 9 | 0.290 | 0.288 |
|  | 2 | 1 | 0 | 14 | 0.156 | 0.155 |
|  | 3 | 1 | 0 | 5 | 0.250 | 0.250 |

According to Table 2, the observed d values estimated from the spots in FIG. 21B or FIG. 21C are almost the same as the theoretical d values of a plurality of plane orientations in $InGaZnO_4$, which means that the In—Ga—Zn oxide film of this comparative example formed by a liquid phase method includes a crystal region due to $InZnGaO_4$.

Therefore, a region which includes periodic atomic arrangement due to $InZnGaO_4$ and a region which has extremely low crystallinity and is close to an amorphous state coexist in the $InZnGaO_4$ film formed by a liquid phase method in spite of the presence of an impurity.

Next, the influence of impurities such as hydrogen and carbon in the metal oxide film of the comparative example on the crystallinity of the metal oxide film was evaluated by calculation.

In the calculation below, the effect of hydrogen on the crystallization of the metal oxide film was examined by the first-principles calculation. Specifically, an energy difference between an amorphous state and a crystal state was measured in both the case where $InGaZnO_4$ does not contain hydrogen and the case where the $InGaZnO_4$ contains hydrogen at 6.67 atom %. An atom density of an In—Ga—Zn—O crystal of $8.54 \times 10^{22}$ atoms/cm$^3$ and the SIMS analysis results shown in FIGS. 18A and 18B indicate that this hydrogen concentration is the same as the hydrogen concentration of the metal oxide film of this comparative example. Note that an In—Ga—Zn oxide film containing In, Ga, and Zn at an atomic ratio of 1:1:1 was used as an example of the metal oxide film for the calculation.

FIG. 22 illustrates a lattice structure of an In—Ga—Zn—O crystal including 112 atoms used for the calculation.

For the calculation, a structure in which no H atom is added to the structure illustrated in FIG. 22 and a structure in which eight H atoms are added to the structure illustrated in FIG. 22 were made, and the structures were optimized. Then, energy was calculated. In addition, amorphous structures were formed on the basis of the optimized structure through the steps below.

(1) Molecular dynamics calculation with an NVT ensemble at 3000 K.
(2) Molecular dynamics calculation with an NVT ensemble at 1000 K for 2 psec.
(3) Optimization of the structures.

Note that three structures were obtained by the above calculation (1) for 5 psec, 5.5 psec, or 6 psec, and then subjected to the calculation (2) and the optimization (3) to form three amorphous structures for each of the three structures. Then, average values of energy were obtained. In the calculation, first principles calculation software "Vienna Ab initio Simulation Package (VASP)" was used. The calculation conditions are shown in Table 3.

TABLE 3

| Steps | Functional | Cutoff Energy (eV) | K Points |
|---|---|---|---|
| (1) | GGA-PBE | 500 | 1 × 1 × 1 |
| (2) | GGA-PBE | 300 | 1 × 1 × 1 |
| (3) | GGA-PBE | 500 | 2 × 2 × 3 |

FIGS. 23A to 23D illustrate part of each structures obtained by the calculation. Table 4 shows the calculation results of the energy difference. FIG. 23A illustrates a structure in which no H atom (0 atom %) is added to a single crystal In—Ga—Zn oxide film. FIG. 23B illustrates a structure in which eight H atoms (6.67 atom %) are added to a single crystal In—Ga—Zn oxide film. FIG. 23C illustrates a structure in which no H atom (0 atom %) is added to an amorphous In—Ga—Zn oxide film FIG. 23D illustrates a structure in which eight H atoms (6.67 atom %) are added to an amorphous In—Ga—Zn oxide film.

TABLE 4

| Hydrogen concentration (atom %) | Density (g/cm$^3$) | Energy difference (amorphous-single crystal) |
|---|---|---|
| 0 | 6.12 | 1.23 |
| 6.67 | 5.82 | 0.54 |

According to Table 4, the energy of the In—Ga—Zn oxide film greatly decreases when the film is crystallized. Further, the stabilization energy due to crystallization decreases when H atoms are added to the film. Accordingly, it is assumed that the observation of the nanobeam electron diffraction pattern similar to a halo pattern in addition to the spot-containing pattern indicating the periodic atomic arrangement in the metal oxide film of this comparative example formed by a liquid phase method is resulted from destabilization of the crystal structure by hydrogen.

As described above, when the metal oxide film contains hydrogen as an impurity, the stability of the crystal is decreased. These calculation results agree with the high concentration of the impurity such as hydrogen and carbon in the metal oxide film of the comparative example, which shows a nanobeam electron diffraction pattern similar to a halo pattern, when compared with the metal oxide film of this embodiment.

This embodiment can be implemented in combination with Embodiment described in this specification as appropriate.

Embodiment 2

In this embodiment, a structural example of a transistor including the metal oxide film which is described as an example in Embodiment 1 and exhibits semiconductor characteristics (an oxide semiconductor film) will be described with reference to drawings.

<Structural Example of Transistor>

Figure 9A:
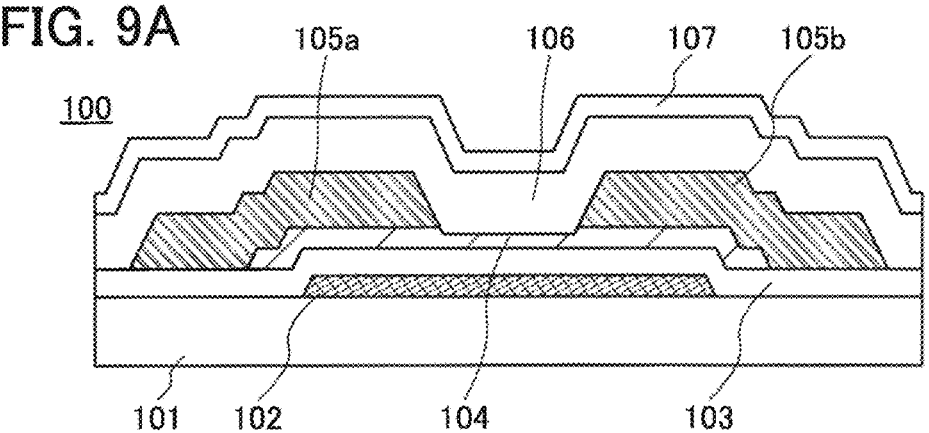
FIGS. 9A to 9C each illustrate a structural example of a transistor in one embodiment.

FIG. 9A is a schematic cross-sectional view of a transistor 100 which is described below as an example. The transistor 100 is a bottom-gate transistor.

The transistor 100 includes a gate electrode 102 provided over a substrate 101, an insulating layer 103 provided over the substrate 101 and the gate electrode 102, an oxide semiconductor layer 104 provided over the insulating layer 103 to overlap with the gate electrode 102, and a pair of electrodes 105a and 105b in contact with the top surface of the oxide semiconductor layer 104. Further, an insulating layer 106 is provided to cover the insulating layer 103, the oxide semiconductor layer 104, and the pair of electrodes 105a and 105b, and an insulating layer 107 is provided over the insulating layer 106.

The oxide semiconductor film of one embodiment of the present invention can be applied to the oxide semiconductor layer 104 in the transistor 100.

<<Substrate 101>>

There is no particular limitation on the property of a material and the like of the substrate 101 as long as the material has heat resistance enough to withstand at least heat treatment which will be performed later. For example, a glass substrate, a ceramic substrate, a quartz substrate, a sapphire substrate, or an yttria-stabilized zirconia (YSZ) substrate may be used as the substrate 101. Alternatively, a single crystal semiconductor substrate or a polycrystalline semiconductor substrate made of silicon, silicon carbide, or the like, a compound semiconductor substrate made of silicon germanium or the like, an SOI substrate, or the like can be used as the substrate 101. Still alternatively, any of these substrates provided with a semiconductor element may be used as the substrate 101.

Still alternatively, a flexible substrate such as a plastic substrate may be used as the substrate 101, and the transistor 100 may be provided directly on the flexible substrate. Further alternatively, a separation layer may be provided between the substrate 101 and the transistor 100. The separation layer can be used when part or the whole of the transistor formed over the separation layer is formed and separated from the substrate 101 and transferred to another substrate. Thus, the transistor 100 can be transferred to a substrate having low heat resistance or a flexible substrate.

<<Gate Electrode 102>>

The gate electrode 102 can be formed using a metal selected from aluminum, chromium, copper, tantalum, titanium, molybdenum, and tungsten; an alloy containing any of these metals as a component; an alloy containing any of these metals in combination; or the like. Further, one or more metals selected from manganese and zirconium may be used. Furthermore, the gate electrode 102 may have a single-layer structure or a stacked-layer structure of two or more layers. For example, a single-layer structure of an aluminum film containing silicon, a two-layer structure in which a titanium film is stacked over an aluminum film, a two-layer structure in which a titanium film is stacked over a titanium nitride film, a two-layer structure in which a tungsten film is stacked over a titanium nitride film, a two-layer structure in which a tungsten film is stacked over a tantalum nitride film or a tungsten nitride film, a three-layer structure in which a titanium film, an aluminum film, and a titanium film are stacked in this order, and the like can be given. Alternatively, an alloy film containing aluminum and one or more metals selected from titanium, tantalum, tungsten, molybdenum, chromium, neodymium, and scandium; or a nitride film of the alloy film may be used.

The gate electrode 102 can also be formed using a light-transmitting conductive material such as indium tin oxide, indium oxide containing tungsten oxide, indium zinc oxide containing tungsten oxide, indium oxide containing titanium oxide, indium tin oxide containing titanium oxide, indium zinc oxide, or indium tin oxide to which silicon oxide is added. It is also possible to have a stacked-layer structure formed using the above light-transmitting conductive material and the above metal.

Further, an In—Ga—Zn-based oxynitride semiconductor film, an In—Sn-based oxynitride semiconductor film, an In—Ga-based oxynitride semiconductor film, an In—Zn-based oxynitride semiconductor film, a Sn-based oxynitride semiconductor film, an In-based oxynitride semiconductor film, a film of metal nitride (such as InN or ZnN), or the like may be provided between the gate electrode 102 and the insulating layer 103. These films each have a work function higher than or equal to 5 eV or higher than or equal to 5.5 eV, which is higher than the electron affinity of the oxide semiconductor. Thus, the threshold voltage of the transistor including an oxide semiconductor can be shifted in the positive direction, and what is called a normally-off switching element can be achieved. For example, an In—Ga—Zn-based oxynitride semiconductor film having a higher nitrogen concentration than at least the oxide semiconductor layer 104, specifically, an In—Ga—Zn-based oxynitride semiconductor film having a nitrogen concentration of 7 atomic % or higher is used.

<<Insulating Layer 103>>

The insulating layer 103 functions as a gate insulating film. The insulating layer 103 in contact with the bottom surface of the oxide semiconductor layer 104 is preferably an amorphous film.

The insulating layer 103 may be formed to have a single-layer structure or a stacked-layer structure using, for example, one or more of silicon oxide, silicon oxynitride, silicon nitride oxide, silicon nitride, aluminum oxide, hafnium oxide, gallium oxide, Ga—Zn-based metal oxide, silicon nitride, and the like.

The insulating layer 103 may be formed using a high-k material such as hafnium silicate ($HfSiO_x$), hafnium silicate to which nitrogen is added ($HfSi_xO_yN_z$), hafnium aluminate to which nitrogen is added ($HfAl_xO_yN_z$), hafnium oxide, or yttrium oxide, so that gate leakage current of the transistor can be reduced.

<<Pair of Electrodes 105a and 105b>>

The pair of electrodes 105a and 105b functions as a source electrode and a drain electrode of the transistor.

The pair of electrodes 105a and 105b can be formed to have a single-layer structure or a stacked-layer structure using, as a conductive material, any of metals such as aluminum, titanium, chromium, nickel, copper, yttrium, zirconium, molybdenum, silver, tantalum, and tungsten, or an alloy containing any of these metals. For example, a single-layer structure of an aluminum film containing silicon, a two-layer structure in which a titanium film is stacked over an aluminum film, a two-layer structure in which a titanium film is stacked over a tungsten film, a two-layer structure in which a copper film is stacked over a copper-magnesium-aluminum alloy film, a three-layer structure in which a titanium film or a titanium nitride film, an aluminum film or a copper film, and a titanium film or a titanium nitride film are stacked in this order, a three-layer structure in which a molybdenum film or a molybdenum nitride film, an aluminum film or a copper film, and a molybdenum film or a molybdenum nitride film are stacked in this order, and the like can be given. Note that a transparent conductive material containing indium oxide, tin oxide, or zinc oxide may be used.

<<Insulating Layer 106, 107>>

The insulating layer 106 is preferably formed using an oxide insulating film containing oxygen at a higher proportion than oxygen in the stoichiometric composition. Such an oxide insulating film releases oxygen upon heating. For instance, when such an oxide insulating film is heated at a temperature that is equal to or higher than a heat treatment temperature in a manufacturing process of a transistor, the amount of released oxygen converted into oxygen atoms is greater than or equal to $1.0 \times 10^{18}$ atoms/cm$^3$, preferably greater than or equal to $3.0 \times 10^{20}$ atoms/cm$^3$ in thermal desorption spectroscopy (TDS) analysis.

As the insulating layer 106, a silicon oxide film, a silicon oxynitride film, or the like can be formed.

Note that the insulating layer 106 also functions as a film which relieves damage to the oxide semiconductor layer 104 at the time of forming the insulating layer 107 later.

An oxide film transmitting oxygen may be provided between the insulating layer 106 and the oxide semiconductor layer 104.

As the oxide film transmitting oxygen, a silicon oxide film, a silicon oxynitride film, or the like can be formed. Note that in this specification, a "silicon oxynitride film" refers to a film that contains oxygen at a higher proportion than nitrogen, and a "silicon nitride oxide film" refers to a film that contains nitrogen at a higher proportion than oxygen.

The insulating layer 107 can be formed using an insulating film having a blocking effect against oxygen, hydrogen, water, and the like. It is possible to prevent outward diffusion of oxygen from the oxide semiconductor layer 104 and entry of hydrogen, water, or the like into the oxide semiconductor layer 104 from the outside by providing the insulating layer 107 over the insulating layer 106. As for such an insulating film, a silicon nitride film, a silicon nitride oxide film, an aluminum oxide film, an aluminum oxynitride film, a gallium oxide film, a gallium oxynitride film, an yttrium oxide film, an yttrium oxynitride film, a hafnium oxide film, and a hafnium oxynitride film can be given as examples.

<Example of Manufacturing Method of Transistor>

Next, an example of a fabrication method of the transistor 100 illustrated in FIGS. 9A to 9C will be described.

Figure 10A:
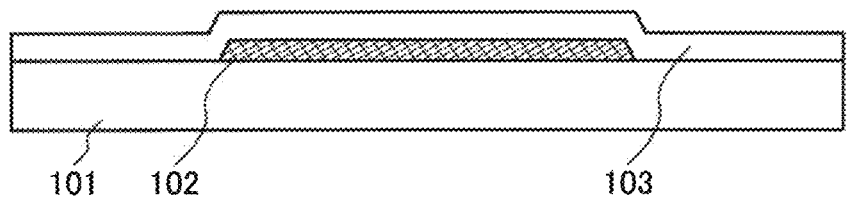
FIGS. 10A to 10D illustrate an example of a method for forming a transistor in one embodiment.

First, as illustrated in FIG. 10A, the gate electrode 102 is formed over the substrate 101, and the insulating layer 103 is formed over the gate electrode 102.

Here, a glass substrate is used as the substrate 101.

<<Formation of Gate Electrode>>

A formation method of the gate electrode 102 is described below. First, a conductive film is formed by a sputtering method, a CVD method, an evaporation method, or the like and then a resist mask is formed over the conductive film using a first photomask by a photolithography process. Then, part of the conductive film is etched using the resist mask to form the gate electrode 102. After that, the resist mask is removed.

Note that instead of the above formation method, the gate electrode 102 may be formed by an electrolytic plating method, a printing method, an ink-jet method, or the like.

<<Formation of Gate Insulating Layer>>

The insulating layer 103 is formed by a sputtering method, a CVD method, an evaporation method, or the like.

In the case where the insulating layer 103 is formed using a silicon oxide film, a silicon oxynitride film, or a silicon nitride oxide film, a deposition gas containing silicon and an oxidizing gas are preferably used as a source gas. Typical examples of the deposition gas containing silicon include silane, disilane, trisilane, and silane fluoride. As the oxidizing gas, oxygen, ozone, dinitrogen monoxide, and nitrogen dioxide can be given as examples.

In the case of forming a silicon nitride film as the insulating layer 103, it is preferable to use a two-step formation method. First, a first silicon nitride film with a small number of defects is formed by a plasma CVD method in which a mixed gas of silane, nitrogen, and ammonia is used as a source gas. Then, a second silicon nitride film in which the hydrogen concentration is low and hydrogen can be blocked is formed by switching the source gas to a mixed gas of silane and nitrogen. With such a formation method, a silicon nitride film with a small number of defects and a blocking property against hydrogen can be formed as the insulating layer 103.

Moreover, in the case of forming a gallium oxide film as the insulating layer 103, a metal organic chemical vapor deposition (MOCVD) method can be employed.

<<Formation of Oxide Semiconductor Layer>>

Figure 10B:
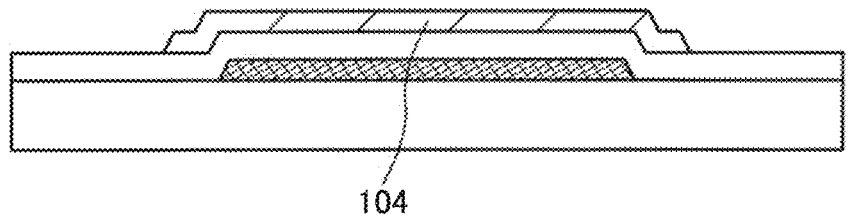

Next, as illustrated in FIG. 10B, the oxide semiconductor layer 104 is formed over the insulating layer 103.

A formation method of the oxide semiconductor layer 104 is described below. First, an oxide semiconductor film is formed using the method described in Embodiment 1. Then, a resist mask is formed over the oxide semiconductor film using a second photomask by a photolithography process. Then, part of the oxide semiconductor film is etched using the resist mask to form the oxide semiconductor layer 104. After that, the resist mask is removed.

After that, heat treatment may be performed. In such a case, the heat treatment is preferably performed under an atmosphere containing oxygen.

<<Formation of Pair of Electrodes>>

Figure 10C:
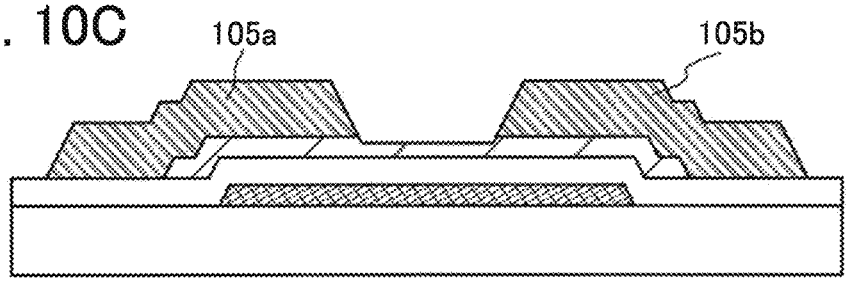

Next, as illustrated in FIG. 10C, the pair of electrodes 105a and 105b is formed.

A formation method of the pair of electrodes 105a and 105b is described below. First, a conductive film is formed by a sputtering method, a CVD method, an evaporation method, or the like. Then, a resist mask is formed over the conductive film using a third photomask by a photolithography process. Then, part of the conductive film is etched using the resist mask to form the pair of electrodes 105a and 105b. After that, the resist mask is removed.

Note that as illustrated in FIG. 10B, an upper part of the oxide semiconductor layer 104 is in some cases partly etched and thinned by the etching of the conductive film. For this reason, the oxide semiconductor layer 104 is preferably formed thick.

<<Formation of Insulating Layer>>

Figure 10D:
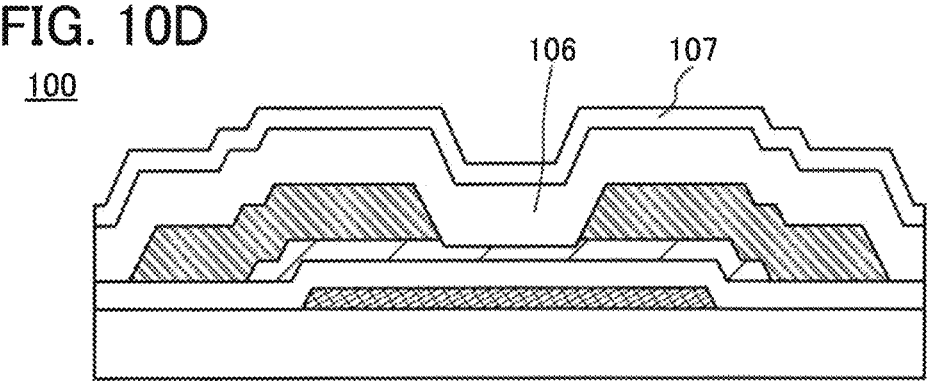

Next, as illustrated in FIG. 10D, the insulating layer 106 is formed over the oxide semiconductor layer 104 and the pair of electrodes 105a and 105b, and the insulating layer 107 is successively formed over the insulating layer 106.

In the case where the insulating layer 106 is formed using a silicon oxide film or a silicon oxynitride film, a deposition gas containing silicon and an oxidizing gas are preferably used as a source gas. Typical examples of the deposition gas containing silicon include silane, disilane, trisilane, and silane fluoride. As the oxidizing gas, oxygen, ozone, dinitrogen monoxide, and nitrogen dioxide can be given as examples.

For example, a silicon oxide film or a silicon oxynitride film is formed under the conditions as follows: the substrate placed in a vacuum-evacuated treatment chamber of a plasma CVD apparatus is held at a temperature higher than or equal to 180° C. and lower than or equal to 260° C., preferably higher than or equal to 200° C. and lower than or equal to 240° C., to the treatment chamber is charged a source gas at a pressure greater than or equal to 100 Pa and less than or equal to 250 Pa, preferably greater than or equal to 100 Pa and less than or equal to 200 Pa, and high-frequency power higher than or equal to 0.17 W/cm$^2$ and lower than or equal to 0.5 W/cm$^2$, preferably higher than or equal to 0.25 W/cm$^2$ and lower than or equal to 0.35 W/cm$^2$ is supplied to an electrode provided in the treatment chamber.

With the application of the high-frequency power, the degradation efficiency of the source gas in plasma is increased, oxygen radicals are increased, and oxidation of the source gas is promoted; therefore, oxygen is contained in the oxide insulating film at a higher proportion than oxygen in the stoichiometric composition. However, the films prepared at the aforementioned substrate temperature release part of oxygen therein upon heating performed in later processes. Thus, it is possible to form an oxide insulating film which contains oxygen at a higher proportion than oxygen in the stoichiometric composition and from which part of oxygen is released by heating.

Further, in the case of providing an oxide insulating film between the oxide semiconductor layer 104 and the insulating layer 106, the oxide insulating film serves as a protective film of the oxide semiconductor layer 104 in the steps of forming the insulating layer 106. Thus, the insulating layer 106 can be formed using the high-frequency power having a high power density while damage to the oxide semiconductor layer 104 is reduced.

For example, a silicon oxide film or a silicon oxynitride film can be formed as the oxide insulating film under the conditions as follows: the substrate placed in a vacuum-evacuated treatment chamber of a plasma CVD apparatus is held at a temperature higher than or equal to 180° C. and lower than or equal to 400° C., preferably higher than or equal to 200° C. and lower than or equal to 370° C., to the treatment chamber is charged a source gas at a pressure greater than or equal to 20 Pa and less than or equal to 250 Pa, preferably greater than or equal to 100 Pa and less than or equal to 250 Pa, and high-frequency power is supplied to an electrode provided in the treatment chamber. Further, when the pressure in the treatment chamber is greater than or equal to 100 Pa and less than or equal to 250 Pa, damage to the oxide semiconductor layer 104 can be reduced.

A deposition gas containing silicon and an oxidizing gas are preferably used as a source gas of the oxide insulating film. Typical examples of the deposition gas containing silicon include silane, disilane, trisilane, and silane fluoride. As the oxidizing gas, oxygen, ozone, dinitrogen monoxide, and nitrogen dioxide can be given as examples.

The insulating layer 107 can be formed by a sputtering method, a CVD method, or the like.

In the case where the insulating layer 107 is formed using a silicon nitride film or a silicon nitride oxide film, a deposition gas containing silicon, an oxidizing gas, and a gas containing nitrogen are preferably used as a source gas. Typical examples of the deposition gas containing silicon include silane, disilane, trisilane, and silane fluoride. As the oxidizing gas, oxygen, ozone, dinitrogen monoxide, and nitrogen dioxide can be given as examples. As the gas containing nitrogen, nitrogen and ammonia can be given as examples.

Through the above process, the transistor 100 can be formed.

Modification Example of Transistor 100

A structural example of a transistor, which is partly different from the transistor 100, will be described below.

Modification Example 1

Figure 9B:
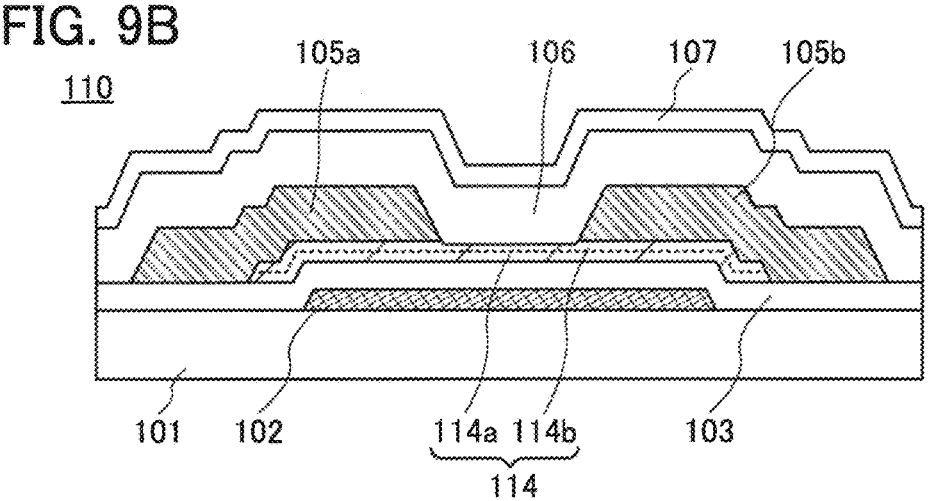

FIG. 9B is a schematic cross-sectional view of a transistor 110 described as an example below. The transistor 110 is different from the transistor 100 in the structure of an oxide semiconductor layer. Note that descriptions of components having structures or functions similar to those of the other structural examples, which are denoted by the same reference numerals, are omitted below.

In an oxide semiconductor layer 114 included in the transistor 110, an oxide semiconductor layer 114a and an oxide semiconductor layer 114b are stacked.

Since a boundary between the oxide semiconductor layer 114a and the oxide semiconductor layer 114b is unclear in some cases, the boundary is shown by a dashed line in FIG. 9B and the like.

The oxide semiconductor film of one embodiment of the present invention can be applied to one or both of the oxide semiconductor layers 114a and 114b.

Typical examples of a material that can be used for the oxide semiconductor layer 114a are an In—Ga oxide, an In—Zn oxide, and an In-M-Zn oxide (M is Al, Ti, Ga, Y, Zr, La, Ce, Nd, or Hf). In the case of using an In-M-Zn oxide for the oxide semiconductor layer 114a, when summation of In and M is assumed to be 100 atomic % and Zn and oxygen are eliminated from consideration, the proportions of In and M are preferably greater than or equal to 25 atomic % and less than 75 atomic %, respectively, and further preferably greater than or equal to 34 atomic % and less than 66 atomic %, respectively. Further, a material having an energy gap of 2 eV or more, preferably 2.5 eV or more, further preferably 3 eV or more is used for the oxide semiconductor layer 114a, for example.

For example, the oxide semiconductor layer 114b contains In or Ga and typically contains an In—Ga oxide, an In—Zn oxide, or In-M-Zn oxide (M is Al, Ti, Ga, Y, Zr, La, Ce, Nd, or Hf). In addition, energy level of the conduction band minimum of the oxide semiconductor layer 114b is closer to the vacuum level than that of the oxide semiconductor layer 114a is. The difference between energy level of the conduction band minimum of the oxide semiconductor layer 114b and energy level of the conduction band minimum of the oxide semiconductor layer 114a is preferably 0.05 eV or more, 0.07 eV or more, 0.1 eV or more, or 0.15 eV or more and 2 eV or less, 1 eV or less, 0.5 eV or less, or 0.4 eV or less.

When an In-M-Zn oxide is used as the oxide semiconductor layer 114b, for example, the atomic ratio between In and M is preferably as follows: the atomic percentage of In is less than 50 atomic % and the atomic percentage of M is greater than or equal to 50 atomic %; further preferably, the atomic percentage of In is less than 25 atomic % and the atomic percentage of M is greater than or equal to 75 atomic %, where summation of In and M is assumed to be 100 atomic % and Zn and oxygen are eliminated from consideration.

For the oxide semiconductor layer 114a, an In—Ga—Zn oxide containing In, Ga, and Zn at an atomic ratio of 1:1:1 or 3:1:2 can be used, for example. Further, for the oxide semiconductor layer 114b, an In—Ga—Zn oxide containing In, Ga, and Zn at an atomic ratio of 1:3:2, 1:6:4, or 1:9:6 can be used. Note that the atomic ratios of the oxide semiconductor layers 114a and 114b can be different from those of the used targets in some cases and there could be a difference of ±20% therebetween.

When an oxide containing a large amount of Ga that serves as a stabilizer is used for the oxide semiconductor layer 114b provided over the oxide semiconductor layer 114a, oxygen can be prevented from being released from the oxide semiconductor layers 114a and 114b.

Note that, without limitation to the compositions and materials described above, a material with an appropriate composition may be used depending on required semiconductor characteristics and electrical characteristics (e.g., field-effect mobility and threshold voltage) of a transistor. Further, in order to obtain required semiconductor characteristics of a transistor, it is preferable that the carrier density, the impurity concentration, the defect density, the atomic ratio of a metal element to oxygen, the interatomic distance, the density, and the like of the oxide semiconductor layers 114a and 114b be set to be appropriate.

Although a structure in which two oxide semiconductor layers are stacked is described above as an example of the oxide semiconductor layer 114, a structure in which three or more oxide semiconductor layers are stacked can also be employed.

Modification Example 2

Figure 9C:
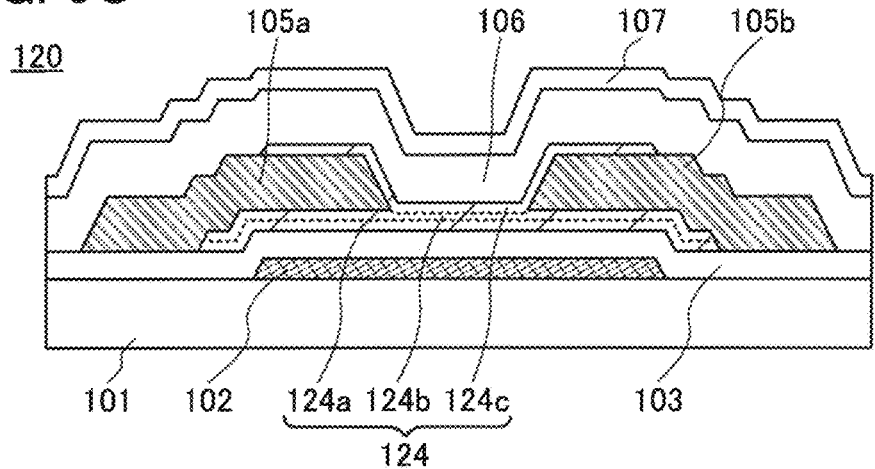

FIG. 9C is a schematic cross-sectional view of a transistor 120 described as an example below. The transistor 120 is different in the structure of an oxide semiconductor layer from the transistor 100 and the transistor 110.

In an oxide semiconductor layer 124 included in the transistor 120, an oxide semiconductor layer 124a, an oxide semiconductor layer 124b, and an oxide semiconductor layer 124c are stacked in this order.

The oxide semiconductor layers 124a and 124b are stacked over the insulating layer 103. The oxide semiconductor layer 124c is provided in contact with the top surface of the oxide semiconductor layer 124b and the top surfaces and side surfaces of the pair of electrodes 105a and 105b.

The oxide semiconductor film of one embodiment of the present invention can be applied to at least one of the oxide semiconductor layers 124a, 124b, and 124c.

The oxide semiconductor layer 124b can have a structure which is similar to that of the oxide semiconductor layer 114a described as an example in Modification Example 1, for example. Further, the oxide semiconductor layers 124a and 124c can each have a structure which is similar to that of the oxide semiconductor layer 114b described as an example in Modification Example 1, for example When an oxide containing a large amount of Ga that serves as a stabilizer is used for the oxide semiconductor layer 124a and the oxide semiconductor layer 124c, for example, oxygen can be prevented from being released from the oxide semiconductor layer 124a, the oxide semiconductor layer 124b, and the oxide semiconductor layer 124c.

In the case where a channel is mainly formed in the oxide semiconductor layer 124b, for example, an oxide containing a large amount of In can be used for the oxide semiconductor layer 124b and the pair of electrodes 105a and 105b is provided in contact with the oxide semiconductor layer 124b; thus, the on-state current of the transistor 120 can be increased.

Another Structure Example of Transistor

A structure example of a top-gate transistor to which the oxide semiconductor film of one embodiment of the present invention can be applied will be described below.

Structural Example

Figure 11A:
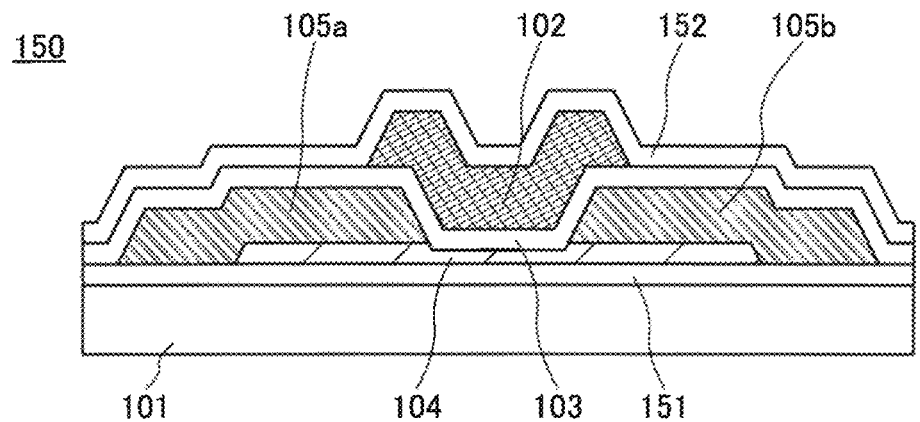
FIGS. 11A to 11C each illustrate a structural example of a transistor in one embodiment.

FIG. 11A is a schematic cross-sectional view of a top-gate transistor 150 which will be described below as an example.

The transistor 150 includes the oxide semiconductor layer 104 provided over the substrate 101 on which an insulating layer 151 is provided, the pair of electrodes 105a and 105b in contact with the top surface of the oxide semiconductor layer 104, the insulating layer 103 provided over the oxide semiconductor layer 104 and the pair of electrodes 105a and 105b, and the gate electrode 102 provided over the insulating layer 103 to overlap with the oxide semiconductor layer 104. Further, an insulating layer 152 is provided to cover the insulating layer 103 and the gate electrode 102.

The oxide semiconductor film of one embodiment of the present invention can be applied to the oxide semiconductor layer 104 in the transistor 150.

The insulating layer 151 has a function of suppressing diffusion of impurities from the substrate 101 to the oxide semiconductor layer 104. For example, a structure similar to that of the insulating layer 107 can be employed. Note that the insulating layer 151 is not necessarily provided.

The insulating layer 152 can be formed using an insulating film having a blocking effect against oxygen, hydrogen, water, and the like in a manner similar to that of the insulating layer 107. Note that the insulating layer 107 is not necessarily provided.

Modification Example

A structural example of a transistor, which is partly different from the transistor 150, will be described below.

Figure 11B:
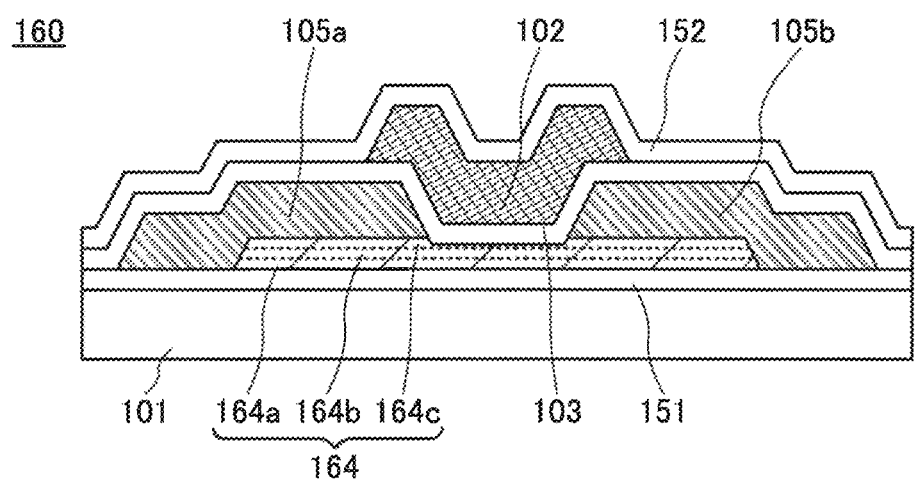

FIG. 11B is a schematic cross-sectional view of a transistor 160 described as an example below. The structure of an oxide semiconductor layer in the transistor 160 is different from that in the transistor 150.

In an oxide semiconductor layer 164 included in the transistor 160, an oxide semiconductor layer 164a, an oxide semiconductor layer 164b, and an oxide semiconductor layer 164c are stacked in this order.

The oxide semiconductor film of one embodiment of the present invention can be applied to at least one of the oxide semiconductor layer 164a, the oxide semiconductor layer 164b, and the oxide semiconductor layer 164c.

The oxide semiconductor layer 164b can have a structure which is similar to that of the oxide semiconductor layer 114a described as an example in Modification Example 1, for example. Further, the oxide semiconductor layers 164a and 164c can each have a structure which is similar to that of the oxide semiconductor layer 114b described as an example in Modification Example 1, for example An oxide containing a large amount of Ga that serves as a stabilizer is used for the oxide semiconductor layer 164a and the oxide semiconductor layer 164c; thus, oxygen can be prevented from being released from the oxide semiconductor layer 164a, the oxide semiconductor layer 164b, and the oxide semiconductor layer 164c.

The oxide semiconductor layer 164 can be formed in the following manner: the oxide semiconductor layer 164c and the oxide semiconductor layer 164b are obtained by etching, so that an oxide semiconductor film to be the oxide semiconductor layer 164a is exposed; and the oxide semiconductor film is processed into the oxide semiconductor layer 164a by a dry etching method. In that case, a reaction product of the oxide semiconductor film is attached to side surfaces of the oxide semiconductor layers 164b and 164c to form a sidewall protective layer (also referred to as a rabbit ear) in some cases. Note that the reaction product is attached by a sputtering phenomenon or at the time of the dry etching.

Figure 11C:
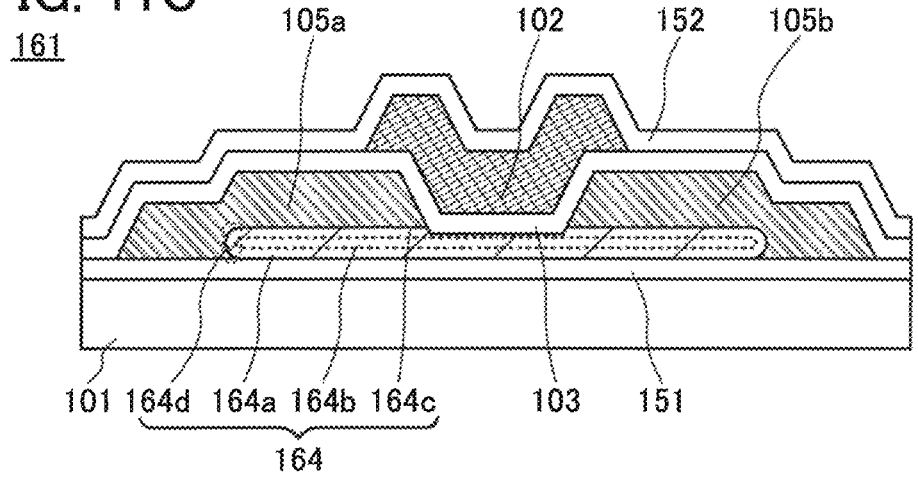

FIG. 11C is a schematic cross-sectional view of a transistor 161 in which a sidewall protective layer 164d is formed as a side surface of the oxide semiconductor layer 164 in the above manner. Note that the other components of the transistor 161 are the same as those of the transistor 160.

The sidewall protective layer 164d mainly contains the same material as the oxide semiconductor layer 164a. In some cases, the sidewall protective layer 164d contains the constituent (e.g., silicon) of a layer provided below the oxide semiconductor layer 164a (the insulating layer 151 here).

With a structure in which a side surface of the oxide semiconductor layer 164b is covered with the sidewall protective layer 164d so as not to be in contact with the pair of electrodes 105a and 105b as illustrated in FIG. 11C, unintended leakage current of the transistor in an off state can be reduced particularly when a channel is mainly formed in the oxide semiconductor layer 164b; thus, a transistor having favorable off-state characteristics can be fabricated. Further, when a material containing a large amount of Ga that serves as a stabilizer is used for the sidewall protective layer 164d, oxygen can be effectively prevented from being released from the side surface of the oxide semiconductor layer 164b; thus, a transistor having excellent stability of electric characteristics can be fabricated.

This embodiment can be implemented in combination with Embodiment described in this specification as appropriate.

Embodiment 3

In this embodiment, a structure of a display panel of one embodiment of the present invention will be described with reference to FIGS. 12A to 12C.

Figure 12A:
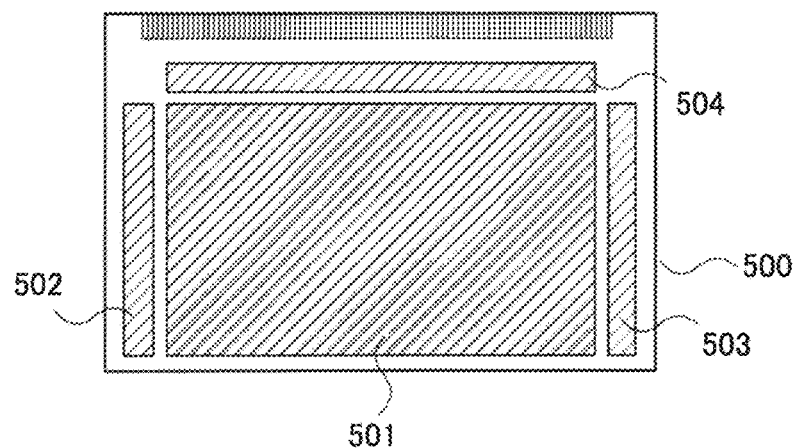
FIGS. 12A to 12C each illustrate a structure of a display panel in one embodiment.

FIG. 12A is a top view of the display panel of one embodiment of the present invention. FIG. 12B illustrates a pixel circuit that can be used in the case where a liquid crystal element is used in a pixel in the display panel of one embodiment of the present invention. FIG. 12C illustrates a pixel circuit that can be used in the case where an organic EL element is used in a pixel in the display panel of one embodiment of the present invention.

The transistor in the pixel portion can be formed in accordance with Embodiment 2. Further, the transistor can be easily formed as an n-channel transistor, and thus part of a driver circuit that can be formed using an n-channel transistor can be formed over the same substrate as the transistor of the pixel portion. With the use of the transistor described in Embodiment 2 for the pixel portion or the driver circuit in this manner, a highly reliable display device can be provided.

FIG. 12A illustrates an example of a block diagram of an active matrix display device. A pixel portion 501, a first scan line driver circuit 502, a second scan line driver circuit 503, and a signal line driver circuit 504 are provided over a substrate 500 in the display device. In the pixel portion 501, a plurality of signal lines extended from the signal line driver circuit 504 are arranged and a plurality of scan lines extended from the first scan line driver circuit 502 and the second scan line driver circuit 503 are arranged. Note that pixels which include display elements are provided in a matrix in respective regions where the scan lines and the signal lines intersect with each other. The substrate 500 of the display device is connected to a timing control circuit (also referred to as a controller or a controller IC) through a connection portion such as a flexible printed circuit (FPC).

In FIG. 12A, the first scan line driver circuit 502, the second scan line driver circuit 503, and the signal line driver circuit 504 are formed over the same substrate 500 as the pixel portion 501. Accordingly, the number of components which are provided outside, such as a drive circuit, can be reduced, so that a reduction in cost can be achieved. Further, in the case where the driver circuit is provided outside the substrate 500, wirings would need to be extended and the number of connections of wirings would be increased, but when the driver circuit is provided over the substrate 500, the number of connections of the wirings can be reduced. Consequently, an improvement in reliability or yield can be achieved.

<Liquid Crystal Panel>

Figure 12B:
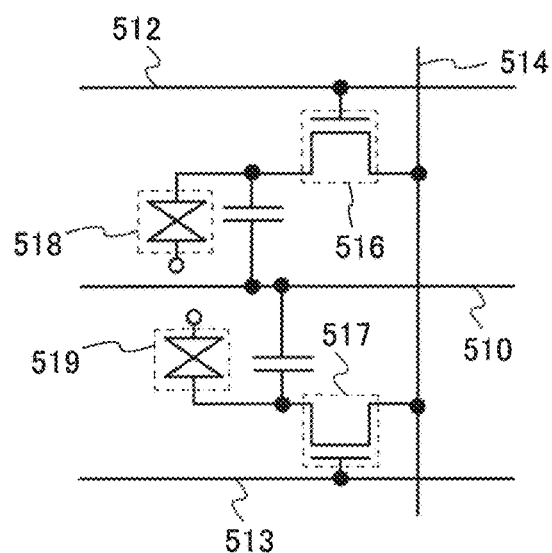

FIG. 12B illustrates an example of a circuit configuration of the pixel. Here, a pixel circuit which is applicable to a pixel of a VA liquid crystal display panel is illustrated.

This pixel circuit can be applied to a structure in which one pixel includes a plurality of pixel electrode layers. The pixel electrode layers are connected to different transistors, and the transistors can be driven with different gate signals. Accordingly, signals applied to individual pixel electrode layers in a multi-domain pixel can be controlled independently.

A gate wiring 512 of a transistor 516 and a gate wiring 513 of a transistor 517 are separated so that different gate signals can be supplied thereto. In contrast, a source or drain electrode 514 functioning as a data line is shared by the transistors 516 and 517. The transistor described in Embodiment 2 can be used as appropriate as each of the transistors 516 and 517. Thus, a highly reliable liquid crystal display panel can be provided.

The shapes of a first pixel electrode layer electrically connected to the transistor 516 and a second pixel electrode layer electrically connected to the transistor 517 are described. The first pixel electrode layer and the second pixel electrode layer are separated by a slit. The first pixel electrode layer has a V shape and the second pixel electrode layer is provided so as to surround the first pixel electrode layer.

A gate electrode of the transistor 516 is connected to the gate wiring 512, and a gate electrode of the transistor 517 is connected to the gate wiring 513. When different gate signals are supplied to the gate wiring 512 and the gate wiring 513, operation timings of the transistor 516 and the transistor 517 can be varied. As a result, alignment of liquid crystals can be controlled.

Further, a storage capacitor may be formed using a capacitor wiring 510, a gate insulating film functioning as a dielectric, and a capacitor electrode electrically connected to the first pixel electrode layer or the second pixel electrode layers.

The multi-domain pixel includes a first liquid crystal element 518 and a second liquid crystal element 519. The first liquid crystal element 518 includes the first pixel electrode layer, a counter electrode layer, and a liquid crystal layer therebetween. The second liquid crystal element 519 includes the second pixel electrode layer, a counter electrode layer, and a liquid crystal layer therebetween.

Note that a pixel circuit of the present invention is not limited to that shown in FIG. 12B. For example, a switch, a resistor, a capacitor, a transistor, a sensor, a logic circuit, or the like may be added to the pixel illustrated in FIG. 12B.

<Organic EL Panel>

Figure 12C:
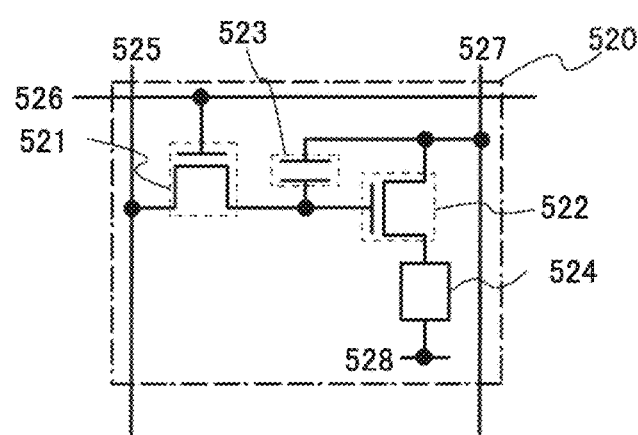

FIG. 12C illustrates another example of a circuit configuration of the pixel portion. Here, a pixel structure of a display panel using an organic EL element is shown.

In an organic EL element, by application of voltage to a light-emitting element, electrons are injected from one of a pair of electrodes and holes are injected from the other of the pair of electrodes, into a layer containing a light-emitting organic compound; thus, current flows. The electrons and holes are recombined, and thus, the light-emitting organic compound is excited. The light-emitting organic compound returns to a ground state from the excited state, thereby emitting light. Owing to such a mechanism, this light-emitting element is referred to as a current-excitation light-emitting element.

FIG. 12C illustrates an applicable example of a pixel circuit. Here, one pixel includes two n-channel transistors. Note that the metal oxide film of one embodiment of the present invention can be used for channel formation regions of the n-channel transistors. Further, digital time grayscale driving can be employed for the pixel circuit.

The configuration of the applicable pixel circuit and operation of a pixel employing digital time grayscale driving will be described.

A pixel 520 includes a switching transistor 521, a driver transistor 522, a light-emitting element 524, and a capacitor 523. A gate electrode layer of the switching transistor 521 is connected to a scan line 526, a first electrode (one of a source electrode layer and a drain electrode layer) of the switching transistor 521 is connected to a signal line 525, and a second electrode (the other of the source electrode layer and the drain electrode layer) of the switching transistor 521 is connected to a gate electrode layer of the driver transistor 522. The gate electrode layer of the driver transistor 522 is connected to a power supply line 527 through the capacitor 523, a first electrode of the driver transistor 522 is connected to the power supply line 527, and a second electrode of the driver transistor 522 is connected to a first electrode (a pixel electrode) of the light-emitting element 524. A second electrode of the light-emitting element 524 corresponds to a common electrode 528. The common electrode 528 is electrically connected to a common potential line provided over the same substrate.

As the switching transistor 521 and the driver transistor 522, the transistor described in Embodiment 2 can be used as appropriate. In this manner, a highly reliable organic EL display panel can be provided.

The potential of the second electrode (the common electrode 528) of the light-emitting element 524 is set to be a low power supply potential. Note that the low power supply potential is lower than a high power supply potential supplied to the power supply line 527. For example, the low power supply potential can be GND, 0V, or the like. The high power supply potential and the low power supply potential are set to be higher than or equal to the forward threshold voltage of the light-emitting element 524, and the difference between the potentials is applied to the light-emitting element 524, whereby current is supplied to the light-emitting element 524, leading to light emission. The forward voltage of the light-emitting element 524 refers to a voltage at which a desired luminance is obtained, and is at least higher than a forward threshold voltage.

Note that gate capacitance of the driver transistor 522 may be used as a substitute for the capacitor 523, so that the capacitor 523 can be omitted. The gate capacitance of the driver transistor 522 may be formed between the channel formation region and the gate electrode layer.

Next, a signal input to the driver transistor 522 is described. In the case of a voltage-input voltage driving method, a video signal for turning on or off the driver transistor 522 without fail is input to the driver transistor 522. In order for the driver transistor 522 to operate in a linear region, voltage higher than the voltage of the power supply line 527 is applied to the gate electrode layer of the driver transistor 522. Note that voltage higher than or equal to voltage which is the sum of power supply line voltage and the threshold voltage Vth of the driver transistor 522 is applied to the signal line 525.

In the case of performing analog grayscale driving, a voltage greater than or equal to a voltage which is the sum of the forward voltage of the light-emitting element 524 and the threshold voltage Vth of the driver transistor 522 is applied to the gate electrode layer of the driver transistor 522. A video signal by which the driver transistor 522 is operated in a saturation region is input, so that current is supplied to the light-emitting element 524. In order for the driver transistor 522 to operate in a saturation region, the potential of the power supply line 527 is set higher than the gate potential of the driver transistor 522. When an analog video signal is used, it is possible to supply current to the light-emitting element 524 in accordance with the video signal and perform analog grayscale driving.

Note that the configuration of the pixel circuit of the present invention is not limited to that shown in FIG. 12C. For example, a switch, a resistor, a capacitor, a sensor, a transistor, a logic circuit, or the like may be added to the pixel circuit illustrated in FIG. 12C.

Embodiment 4

In this embodiment, structures of a semiconductor device including the metal oxide film of one embodiment of the present invention and electronic devices will be described with reference to FIG. 13 and FIGS. 14A to 14D.

Figure 13:
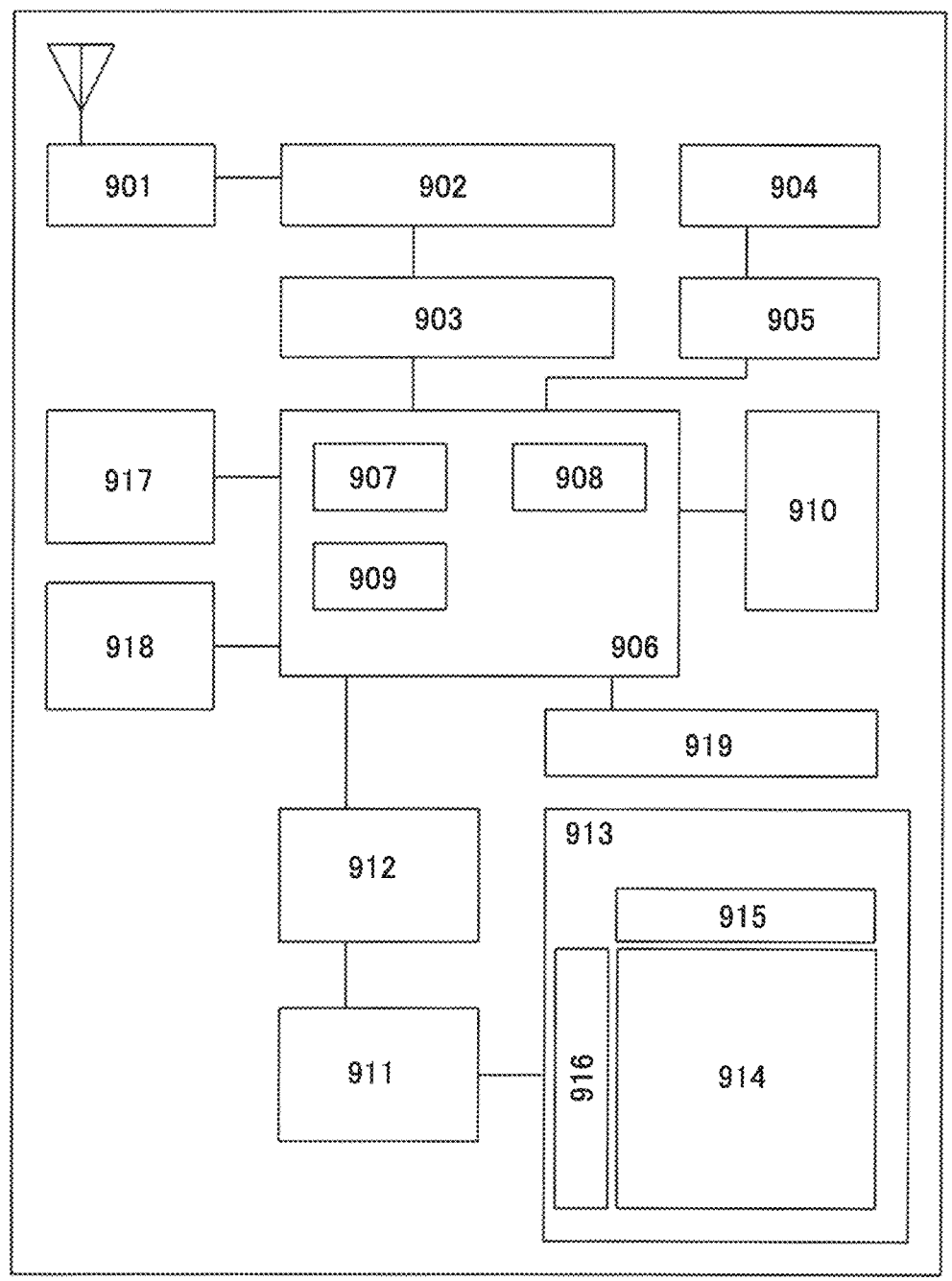
FIG. 13 is a block diagram of an electronic device in one embodiment.

FIG. 13 is a block diagram of an electronic device including the semiconductor device to which the metal oxide film of one embodiment of the present invention is applied.

FIGS. 14A to 14D are external views of electronic devices each including the semiconductor device to which the metal oxide film of one embodiment of the present invention is applied.

An electronic device illustrated in FIG. 13 includes an RF circuit 901, an analog baseband circuit 902, a digital baseband circuit 903, a battery 904, a power supply circuit 905, an application processor 906, a flash memory 910, a display controller 911, a memory circuit 912, a display 913, a touch sensor 919, an audio circuit 917, a keyboard 918, and the like.

The application processor 906 includes a CPU 907, a DSP 908, and an interface (IF) 909. Moreover, the memory circuit 912 can include an SRAM or a DRAM.

The transistor described in Embodiment 2 is applied to the memory circuit 912, whereby a highly reliable electronic device which can write and read data can be provided.

The transistor described in Embodiment 2 is applied to a register or the like included in the CPU 907 or the DSP 908, whereby a highly reliable electronic device which can write and read data can be provided.

Note that in the case where the off-state leakage current of the transistor described in Embodiment 2 is extremely small, the memory circuit 912 can store data for a long time and can have sufficiently reduced power consumption. Moreover, the CPU 907 or the DSP 908 can store the state before power gating in a register or the like during a period in which the power gating is performed.

Further, the display 913 includes a display portion 914, a source driver 915, and a gate driver 916.

The display portion 914 includes a plurality of pixels arranged in a matrix. The pixel includes a pixel circuit, and the pixel circuit is electrically connected to the gate driver 916.

The transistor described in Embodiment 2 can be used as appropriate in the pixel circuit or the gate driver 916. Accordingly, a highly reliable display can be provided.

Examples of electronic devices are a television set (also referred to as a television or a television receiver), a monitor of a computer or the like, a camera such as a digital camera or a digital video camera, a digital photo frame, a mobile phone handset (also referred to as a mobile phone or a mobile phone device), a portable game machine, a portable information terminal, an audio reproducing device, a large-sized game machine such as a pachinko machine, and the like.

Figure 14A:
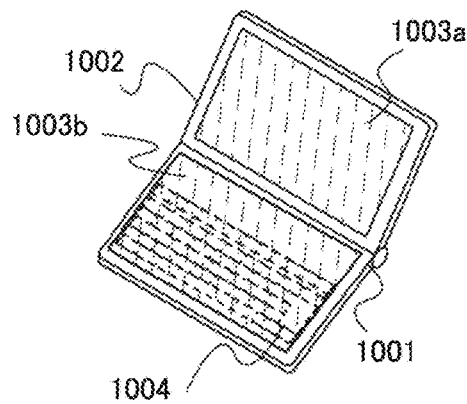
FIGS. 14A to 14D are each an external view of an electronic device in one embodiment.

FIG. 14A illustrates a portable information terminal, which includes a main body 1001, a housing 1002, a display portion 1003a, a display portion 1003b, and the like. The display portion 1003b includes a touch panel. By touching a keyboard button 1004 displayed on the display portion 1003b, screen operation can be carried out, and text can be input. Needless to say, the display portion 1003a may functions as a touch panel. A liquid crystal panel or an organic light-emitting panel is fabricated by using the transistor described in Embodiment 2 as a switching element and applied to the display portion 1003a or 1003b, whereby a highly reliable portable information terminal can be provided.

The portable information terminal illustrated in FIG. 14A can have a function of displaying a variety of kinds of data (e.g., a still image, a moving image, and a text image), a function of displaying a calendar, a date, the time, or the like on the display portion, a function of operating or editing data displayed on the display portion, a function of controlling processing by a variety of kinds of software (programs), and the like. Further, an external connection terminal (an earphone terminal, a USB terminal, or the like), a recording medium insertion portion, or the like may be provided on the back surface or the side surface of the housing.

The portable information terminal illustrated in FIG. 14A may transmit and receive data wirelessly. Through wireless communication, desired book data or the like can be purchased and downloaded from an electronic book server.

Figure 14B:
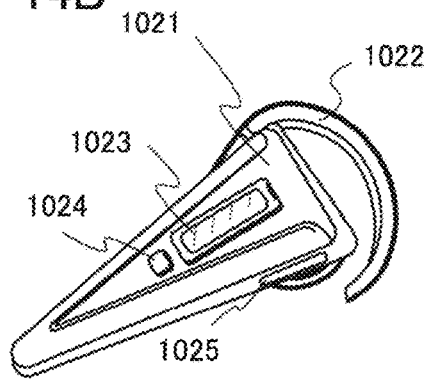

FIG. 14B illustrates a portable music player including, in a main body 1021, a display portion 1023, a fixing portion 1022 with which the portable music player can be worn on the ear, a speaker, an operation button 1024, an external memory slot 1025, and the like. A liquid crystal panel or an organic light-emitting panel is fabricated by using the transistor described in Embodiment 2 as a switching element and applied to the display portion 1023, whereby a highly reliable portable music player can be provided.

Furthermore, when the portable music player illustrated in FIG. 14B has an antenna, a microphone function, or a wireless communication function and is used with a mobile phone, a user can talk on the phone wirelessly in a hands-free way while driving a car or the like.

Figure 14C:
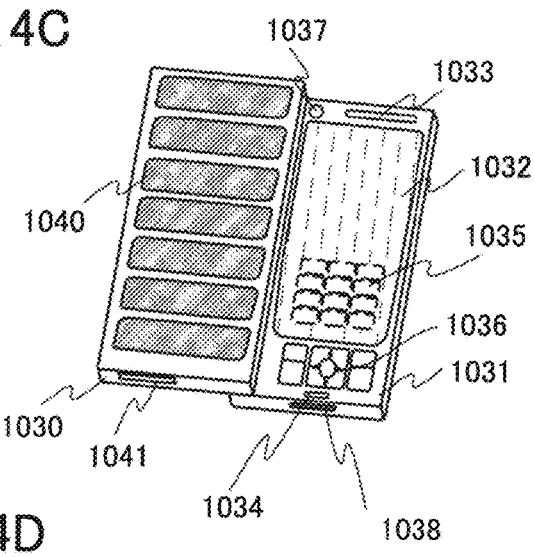

FIG. 14C illustrates a mobile phone which includes two housings, a housing 1030 and a housing 1031. The housing 1031 includes a display panel 1032, a speaker 1033, a microphone 1034, a pointing device 1036, a camera lens 1037, an external connection terminal 1038, and the like. The housing 1030 is provided with a solar cell 1040 for charging the mobile phone, an external memory slot 1041, and the like. In addition, an antenna is incorporated in the housing 1031. The transistor described in Embodiment 2 is applied to the display panel 1032, whereby a highly reliable mobile phone can be provided.

Further, the display panel 1032 includes a touch panel. A plurality of operation keys 1035 which are displayed as images are indicated by dotted lines in FIG. 14C. Note that a boosting circuit by which a voltage output from the solar cell 1040 is increased so as to be sufficiently high for each circuit is also included.

For example, a power transistor used for a power supply circuit such as a boosting circuit can also be formed when the metal oxide film of the transistor described in the Embodiment 2 has a thickness greater than or equal to 2 μm and less than or equal to 50 μm.

In the display panel 1032, the direction of display is changed as appropriate depending on the application mode. Further, the mobile phone is provided with the camera lens 1037 on the same surface as the display panel 1032, and thus it can be used as a video phone. The speaker 1033 and the microphone 1034 can be used for videophone calls, recording, and playing sound, and the like as well as voice calls. Moreover, the housings 1030 and 1031 in a state where they are developed as illustrated in FIG. 14C can shift, by sliding, to a state where one is lapped over the other. Therefore, the size of the mobile phone can be reduced, which makes the mobile phone suitable for being carried around.

The external connection terminal 1038 can be connected to an AC adaptor and a variety of cables such as a USB cable, whereby charging and data communication with a personal computer or the like are possible. Further, by inserting a recording medium into the external memory slot 1041, a larger amount of data can be stored and moved.

Further, in addition to the above functions, an infrared communication function, a television reception function, or the like may be provided.

Figure 14D:
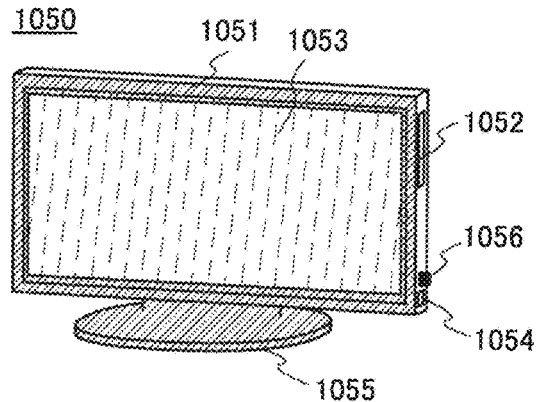

FIG. 14D illustrates an example of a television set. In a television set 1050, a display portion 1053 is incorporated in a housing 1051. Images can be displayed on the display portion 1053. Moreover, a CPU is incorporated in a stand 1055 for supporting the housing 1051. The transistor described in Embodiment 2 is applied to the display portion 1053 and the CPU, whereby the television set 1050 can be highly reliable.

The television set 1050 can be operated with an operation switch of the housing 1051 or a separate remote controller. Further, the remote controller may be provided with a display portion for displaying data output from the remote controller.

Note that the television set 1050 is provided with a receiver, a modem, and the like. With the use of the receiver, the television set 1050 can receive general TV broadcasts. Moreover, when the television set 1050 is connected to a communication network with or without wires via the modem, one-way (from a sender to a receiver) or two-way (between a sender and a receiver or between receivers) information communication can be performed.

Further, the television set 1050 is provided with an external connection terminal 1054, a storage medium recording and reproducing portion 1052, and an external memory slot. The external connection terminal 1054 can be connected to various types of cables such as a USB cable, whereby data communication with a personal computer or the like is possible. A disk storage medium is inserted into the storage medium recording and reproducing portion 1052, and reading data stored in the storage medium and writing data to the storage medium can be performed. In addition, an image, a video, or the like stored as data in an external memory 1056 inserted into the external memory slot can be displayed on the display portion 1053.

Further, in the case where the off-state leakage current of the transistor described in Embodiment 2 is extremely small, when the transistor is applied to the external memory 1056 or the CPU, the television set 1050 can have high reliability and sufficiently reduced power consumption.

EXPLANATION OF REFERENCE

100: transistor, 101: substrate, 102: gate electrode, 103: insulating layer, 104: oxide semiconductor layer, 105*a*: electrode, 105*b*: electrode, 106: insulating layer, 107: insulating layer, 110: transistor, 114: oxide semiconductor layer, 114*a*: oxide semiconductor layer, 114*b*: oxide semiconductor layer, 120: transistor, 124: oxide semiconductor layer, 124*a*: oxide semiconductor layer, 124*b*: oxide semiconductor layer, 124*c*: oxide semiconductor layer, 150: transistor, 151: insulating layer, 152: insulating layer, 160: transistor, 161: transistor, 164: oxide semiconductor layer, 164*a*: oxide semiconductor layer, 164*b*: oxide semiconductor layer, 164*c*: oxide semiconductor layer, 164*d*: sidewall protective layer, 200: quartz glass substrate, 202: dummy substrate, 204: metal oxide film, 210*a*: region, 210*b*: region, 500: substrate, 501: pixel portion, 502: scan line driver circuit, 503: scan line driver circuit, 504: signal line driver circuit, 510: capacitor wiring, 512: gate wiring, 513: gate wiring, 514: drain electrode, 516: transistor, 517: transistor, 518: liquid crystal element, 519: liquid crystal element, 520: pixel, 521: switching transistor, 522: driver transistor, 523: capacitor, 524: light-emitting element, 525: signal line, 526: scan line, 527: power supply line, 528: common electrode, 901: RF circuit, 902: analog baseband circuit, 903: digital baseband circuit, 904: battery, 905: power supply circuit, 906: application processor, 907: CPU, 908: DSP, 910: flash memory, 911: display controller, 912: memory circuit, 913: display, 914: display portion, 915: source driver, 916: gate driver, 917: audio circuit, 918: keyboard, 919: touch sensor, 1001: main body, 1002: housing, 1003*a*: display portion, 1003*b*: display portion, 1004: keyboard button, 1021: main body, 1022: fixing portion, 1023: display portion, 1024: operation button, 1025: external memory slot, 1030: housing, 1031: housing, 1032: display panel, 1033: speaker, 1034: microphone, 1035: operation key, 1036: pointing device, 1037: camera lens, 1038: external connection terminal, 1040: solar cell, 1041: external memory slot, 1050: television set, 1051: housing, 1052: storage medium recording and reproducing portion, 1053: display portion, 1054: external connection terminal, 1055: stand, and 1056: external memory.

This application is based on Japanese Patent Application serial no. 2012-245992 filed with Japan Patent Office on Nov. 8, 2012, Japanese Patent Application serial no. 2013-016242 filed with Japan Patent Office on Jan. 30, 2013, and Japanese Patent Application serial no. 2013-056768 filed with Japan Patent Office on Mar. 19, 2013, the entire contents of which are hereby incorporated by reference.

The invention claimed is:

1. A method for manufacturing a metal oxide film comprising:

forming the metal oxide film by a sputtering method using a sputtering target comprising a polycrystalline oxide in an atmosphere where oxygen partial pressure is greater than or equal to 33%, wherein the sputtering target comprises indium, gallium and zinc, wherein the metal oxide film comprises a plurality of crystal parts when the metal oxide film is formed, wherein a size of one of the plurality of crystal parts is less than or equal to 10 nm, and wherein a crystal peak is not observable in an XRD spectrum with respect to the metal oxide film.

2. The method for manufacturing a metal oxide film according to claim 1, wherein the size of the one of the plurality of crystal parts is less than or equal to 5 nm.

3. The method for manufacturing a metal oxide film according to claim 1, wherein the XRD spectrum is measured by an out-of-plane method.

4. The method for manufacturing a metal oxide film according to claim 1, wherein the metal oxide film is formed without heating a substrate on which the metal oxide film is formed.

5. The method for manufacturing a metal oxide film according to claim 1, further comprising, performing a first heat treatment in an atmosphere comprising nitrogen, and performing a second heat treatment in an atmosphere comprising nitrogen and oxygen.

6. A method for manufacturing a metal oxide film comprising:

forming the metal oxide film by a sputtering method using a sputtering target comprising a polycrystalline oxide in an atmosphere where oxygen partial pressure is greater than or equal to 33%, wherein the sputtering target comprises indium, gallium and zinc, wherein the metal oxide film comprises a crystal part when the metal oxide film is formed, wherein a size of the crystal part is less than or equal to 10 nm, wherein a crystal peak is not observable in an XRD spectrum with respect to the metal oxide film, and wherein a plurality of circumferentially distributed spots are observable in a measurement area greater than or equal to an area with a diameter of 5 nmφ and less than or equal to an area with a diameter of 10 nmφ in a nanobeam electron diffraction pattern of a cross-section of the metal oxide film.

7. The method for manufacturing a metal oxide film according to claim 6, wherein there is no difference between the first plurality of circumferentially distributed spots and a second plurality of circumferentially distributed spots which are observable in a nanobeam electron diffraction of a cross-section in which a measurement area is 5 nmϕ or more and 10 nmϕ or less with respect to the same metal oxide film after being irradiated with an electron beam whose beam diameter is converged to about 1 nmϕ for one minute.

8. The method for manufacturing a metal oxide film according to claim 7,
wherein an acceleration voltage for the electron beam is 200 kV.

9. The method for manufacturing a metal oxide film according to claim 6,
wherein the size of the crystal part is less than or equal to 5 nm.

10. The method for manufacturing a metal oxide film according to claim 6,
wherein the XRD spectrum is measured by an out-of-plane method.

11. The method for manufacturing a metal oxide film according to claim 6,
wherein the metal oxide film is formed without heating a substrate on which the metal oxide film is formed.

12. The method for manufacturing a metal oxide film according to claim 6, further comprising,
performing a first heat treatment in an atmosphere comprising nitrogen, and
performing a second heat treatment in an atmosphere comprising nitrogen and oxygen.

13. A method for manufacturing a metal oxide film comprising:
forming the metal oxide film by a sputtering method using a sputtering target comprising a polycrystalline oxide in an atmosphere where oxygen partial pressure is greater than or equal to 33%,
wherein the sputtering target comprises indium, gallium and zinc,
wherein the metal oxide film comprises a crystal part when the metal oxide film is formed,
wherein a size of the crystal part is less than or equal to 10 nm,
wherein a crystal peak is not observable in an XRD spectrum with respect to the metal oxide film,
wherein a plurality of circumferentially distributed spots are observable in a measurement area greater than or equal to an area with a diameter of 5 nmϕ and less than or equal to an area with a diameter of 10 nmϕ in a nanobeam electron diffraction pattern of a cross-section of the metal oxide film, and
wherein a halo pattern is observable in a selected-area electron diffraction pattern of a plane of the metal oxide film.

14. The method for manufacturing a metal oxide film according to claim 13,
wherein there is no difference between the first plurality of circumferentially distributed spots and a second plurality of circumferentially distributed spots which are observable in a nanobeam electron diffraction of a cross-section in which a measurement area is 5 nmϕ or more and 10 nmϕ or less with respect to the same metal oxide film after being irradiated with an electron beam whose beam diameter is converged to about 1 nmϕ for one minute.

15. The method for manufacturing a metal oxide film according to claim 14,
wherein an acceleration voltage for the electron beam is 200 kV.

16. The method for manufacturing a metal oxide film according to claim 13,
wherein the size of the crystal part is less than or equal to 5 nm.

17. The method for manufacturing a metal oxide film according to claim 13,
wherein the XRD spectrum is measured by an out-of-plane method.

18. The method for manufacturing a metal oxide film according to claim 13,
wherein the metal oxide film is formed without heating a substrate on which the metal oxide film is formed.

19. The method for manufacturing a metal oxide film according to claim 13, further comprising,
performing a first heat treatment in an atmosphere comprising nitrogen, and
performing a second heat treatment in an atmosphere comprising nitrogen and oxygen.

\* \* \* \* \*